United States Patent [19]

Singer et al.

[11] Patent Number: 4,888,278
[45] Date of Patent: Dec. 19, 1989

[54] IN-SITU HYBRIDIZATION TO DETECT NUCLEIC ACID SEQUENCES IN MORPHOLOGICALLY INTACT CELLS

[75] Inventors: Robert H. Singer, Shrewsbury, Mass.; Jeanne B. Lawrence, Mapleville, R.I.

[73] Assignee: University of Massachusetts Medical Center, Worcester, Mass.

[21] Appl. No.: 257,198

[22] Filed: Oct. 13, 1988

Related U.S. Application Data

[63] Continuation of Ser. No. 790,107, Oct. 22, 1985, abandoned.

[51] Int. Cl.$^4$ .................. C12N 15/00; G01N 33/566; G01N 33/552
[52] U.S. Cl. ......................... 435/6; 435/810; 436/501; 436/504; 436/527; 436/528; 935/2; 935/4; 935/9; 935/78
[58] Field of Search ...................... 435/5, 91

[56] References Cited

U.S. PATENT DOCUMENTS 4,419,446 12/1983 Howley et al. .................. 435/91 X
4,652,517 3/1987 Scholl et al. ............................ 435/5

OTHER PUBLICATIONS

Godard, C. M., et al., "Improved Method . . . in situ Hybridization", Chem. Abst 92(25), 211254y (1980).
Leary, J. J. et al., "Rapid and Sensitive Method . . . Biotiu-Labeled DNA Probes . . . ", Proc. Natl. Acad. Sci USA 80, 4045–4049 (Jul. 1983).
Kuo, M. T. et al., "Location of Messenger Specifying Sequences . . . ", Chem. Abst. 88(1), 3872p (1978).
Brandsma et al., "Nucleic Acid Spot Hybridization . . . ", Proc. Natl. Acad. Sci. USA 77, 6851–6855 (Nov. 1980).
Godard, C. M. et al., "Improved Method for Detection of Cellular Transcripts by in situ Hybridization . . . ", Histochem 65, 291–300 (1980).
Lawrence et al., "Methodological Analysis of in-situ Hybridization to Cellular RNA Using Double-Stranded DNA Probes", J. Cell Biology, vol. 99: Abstract No. 519, p. 141a (Oct. 1984).
Singer et al., "Actin Gene Expression Visualized in Chicken Muscle Tissue Culture by Using in-situ Hybridization . . . Analog", Proc. Natl. Acad. Sci. USA, vol. 79, pp. 7331–7335 (1982).
Gee et al., "In-Situ Hybridization Histochmistry: A Technique for the Study of Gene Expression in Single Cells", DNA, vol. 2, No. 2, pp. 157–163 (1983).
Capco et al., "Differential Distribution of Poly(A)–Containing RNA in the Embryonic Cells of Oncopeltus Fasciatus", Developmental Biology, 67: 137–151 (1978).
Angerer et al., "Detection of Poly A+ in Sea Urchin Embryos by Quantitative in situ Hybridization", Nucleic Acids Research, vol. 9, No. 12, pp. 2819–2839 (1981)

Primary Examiner—Robert J. Warden
Assistant Examiner—Richard Wagner
Attorney, Agent, or Firm—Hamilton, Brook, Smith & Reynolds

[57] ABSTRACT

Improved methodologies for in-situ hybridization and detection of hybridized nucleic acid sequences in cell cultures and tissue sections are provided which offer an increase of speed, sensitivity, and simplicity unavailable in previously known techniques. The invention detects specific nucleic acids of interest, particularly RNA sequences, within cells and tissues utilizing DNA of a particular size as a probe to find those sequences which are held substantially in common between the cell or tissue and the probe. The cells are fixed preferably in paraformaldehyde and then hybridized using a hybridization fluid for not less than 10 minutes but not substantially more than 24 hours. A variety of identifying labels are attached to the probe which permit quick and rapid detection via measurement of radioactive isotope decay or by colorimetric detection of enzymatic reaction products. The invention is intended for use as a diagnostic kit in clinical/diagnostic laboratory testing facilities in that it permits a relatively unskilled person to accurately and reproducibly detect a few molecules of a specific nucleic acid of interest in-situ in 10 minutes.

3 Claims, 7 Drawing Sheets

IN-SITU HYBRIDIZATION TO DETECT NUCLEIC ACID SEQUENCES IN MORPHOLOGICALLY INTACT CELLS

This is a continuation of co-pending application Ser. No. 06/790,107 filed on Oct. 22, 1985 now abandoned.

FIELD OF THE INVENTION

The present invention is concerned generally with improved methodologies for hybridization of nucleic acids within cells and tissues and methods for detection of such hybridization, and is specifically directed to improved in-situ hybridization methods and detection techniques for quantitative identification and analysis of specific nucleic acid sequences within whole cells and/or tissues.

Hybridization is a general technique in which the complementary strands of deoxyribonucleic acid (hereinafter "DNA") molecules, ribonucleic acid (hereinafter "RNA") molecules, and combinations of DNA and RNA are separated into single strands and then allowed to renature or reanneal and reform base-paired double helices. At least three major classes of hybridization are presently known and used: solution hybridization which disrupts the individual cells and extracts the internal nucleic acids into solution prior to hybridization; filter or blot hybridization which transfers extracted DNA (or RNA) fragments from agarose gels to filters or blotters such as cellulose nitrate for subsequent hybridization with radioactive RNA and then detects the amount of hybridization by radioautography or fluorography; and in-situ hybridization which makes possible the detection and localization of specific nucleic acid sequences directly within an intact cell or tissue without any extraction of nucleic acids whatsoever. Although each of these respective hybridization techniques often employ cells, tissues, and certain reagents in common, each technique is generally viewed and accepted within this art as different and completely distinguishable from any other.

In-situ hybridization is a technique which yields both molecular and morphological information about intact individual cells. Rather than requiring the investigator to laboriously extract DNA and/or RNA from a heterogeneous cell population, the technique permits detection of DNA and RNA in-situ and allows the investigator to identify those particular cells which contain specific DNA or RNA sequences of interest. This technique also allows one to determine simultaneously the biochemical and/or morphological characteristics of these cells. For this reason, the in-situ hybridization methodology has direct application for many areas of biomedical and clinical research including developmental biology, cell biology, genetics, clinical diagnosis, and pathological evaluation. Not only does this technique make possible the investigation of expression of a single gene within a single cell, but it also allows for the detection of a specific DNA or RNA of interest such as those found in a viral genome within the various kinds of cells or tissues. Thus, in combination with the presently available recombinant DNA technology whereby individual nucleotide sequences can be precisely defined, in-situ hybridization becomes a major tool for elucidating the molecular mechanisms for disease etiology or the pathology of various diseases and disorders.

Despite the potential of in-situ hybridization as a molecular analytical technique, the development of specific protocols and procedures has been largely haphazard and disjointed. Since first described in 1969 by Gall et al. [*P.N.A.S. U.S.A.* 63:378–383 (1969); *Methods In Enzymol.* 38:470–480 (1971)], the in-situ approach has been used primarily for the localization of specific DNA sequences such as the mapping of genes to Drosophila polytene chromosomes. In more recent years, cytological hybridization has begun to be applied to the investigation of cellular RNA to obtain molecular information concerning the primary products of gene expression. These developments are exemplified by the following publications: Harrison et al., *J. Cell Biol.* 165:54–59 (1974); John et al., *Cell* 21:501–508 (1977); Brahic and Haase, *P.N.A.S. USA* 75:6125–6129 (1978); Capco and Jeffrey, *Devel. Biol.* 67:137–151 (1978); Angerer et al., *Nucleic Acids Res.* 9:2819–2840 (1981); Venezky et al., *Cell* 24:385–391 (1981); Singer and Ward, *P.N.A.S. USA* 79:731–7335 (1982); McAllister et al., *Science* 222:800–808 (1983); Edwards and Wood, *Dev. Biol.* 97:375–390 (1983); Moon et al., *Devel. Biol.* 95:447–458 (1983); Hafen et al., *EMBO J.* 2:617–623 (1983); Cox et al., *Devel. Biol.* 101:485–502 (1984); Langer et al., *Proc. Natl. Acad. Sci. USA* 78:6633–6637 (1981); Leary et al., *Proc. Natl. Acad. Sci. USA* 80:4045–4049 (1983); and the references identified within each of these respective publications.

Despite the extensive investigations described within these publications, the presently available in-situ hybridization techniques share a large number of defects and deficiencies in common, many of which have not been appreciated, investigated, or explored in detail previously. For example, the development and application of in-situ hybridization has been largely qualitative rather than quantitative in nature; although several investigators have developed a quantitative approach using autoradiography on cells to which a probe has been hybridized [Gee and Roberts, *DNA* 2:157–163 (1983)], all of the described methods are limited to testing only a very few samples at one time and are enormously time consuming and laborious. Equally important, the critical protocol parameters such as choice of fixation, the need for cell pretreatment, the size of the probes utilized, the concentration of probe and the time required for hybridization, vary markedly among the different protocols. Moreover, the presently known protocols are highly complex procedures requiring many manipulative steps, many of which are destructive to the cell by their ability to dissociate the cellular components such as cellular RNA and the general morphology and integrity of the cell. Overall therefore, the presently known detection methods are widely divergent protocols which are uniformly time consuming and laborious; do not allow for extensive analysis or detection of critical parameters within any single procedure; and do not permit testing of large numbers of samples. Most importantly, the protocols vary extensively in their general effectiveness and reproducibility. For these many reasons, there remains a generally recognized and continuing need within this art for a rationally derived in-situ hybridization methodology and detection methodology having a simplified, efficient protocol that is rapid, sensitive, and reproducible such that a relatively unskilled person can perform it and yet remains non-destructive to cellular nucleic acids and cell morphology.

SUMMARY OF THE INVENTION

The present invention provides a rapid method for in-situ hybridization and several rapid methods for detecting a specific nucleic acid of interest in one or more test samples. The novel in-situ hybridization method comprises the steps of obtaining at least one sample containing tissues or cells; fixing the sample using a fixative which preferably preserves and retains the nucleic acids of the cellular matrix such that the sample remains substantially in a condition for probe penetration; preferably avoiding proteolytic pretreatment of the sample; preparing a hybridization fluid comprising a labeled probe having at least one predetermined nucleotide sequence and an identifying label, this labeled probe ranging from about 20-4000 nucleotides in size; and combining the hybridization fluid with the fixed sample for not substantially less than 10 minutes and not substantially more than 24 hours.

The method for detecting a specific nucleic acid of interest within a sample comprises the steps of: obtaining at least one sample containing cells or tissues whose cellular nucleic acids have been hybridized in-situ using a radiolabeled probe comprising a predetermined nucleotide sequence and a radionuclide; and detecting the amount of radiolabel retained within the sample by radiation counting, the amount of radiolabeled probe retained by the sample being a measure of the nucleic acids of interest present within the sample which are substantially similar in composition to the predetermined nucleotide sequences of the probe.

Another rapid detection method is also provided which utilizes the affinity binding proteins of biotin and avidin to detect a specific nucleic acid of interest within a hybridized sample using an enzymatic detection procedure. Both the in-situ hybridization method and the rapid detection methods may be performed by employing diagnostic kits whose prepared reagents are utilized in the above-described manner to provide in-situ hybridizations and detection of labeled probes with speed, efficiency, accuracy, and without substantial cellular destruction or changes in cell morphology.

DETAILED DESCRIPTION OF THE DRAWING

The present invention may be more fully and easily understood when taken in conjunction with the accompanying drawing, in which.

DETAILED DESCRIPTION OF THE INVENTION

Figure 1:
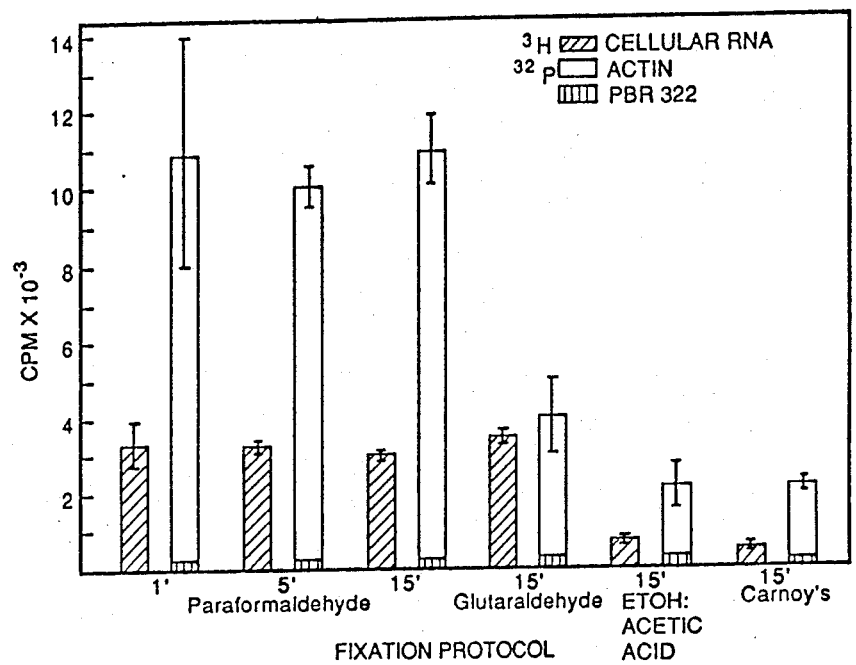
FIG. 1 is a graph illustrating the effects of the fixation protocol on cellular RNA retention and on hybridization.

The novel and unique in-situ hybridization method and detection methodologies described herein are protocols which allow the use of recombinant DNA (or RNA) probes with cells, microorganisms, or tissues whose structures are compatible with microscopic examination such as is routinely performed in bacteriology, histology or pathology laboratories. The present invention applies a DNA probe of predetermined nucleotide sequence to the sample cells (or tissues) and then examines the sample by microscopy to determine how many or in which type of cells (or tissues) within the population contain the specific nucleic acids of interest. Thus, for cells (or tissues) expressing a particular gene, the products of that gene and the RNA responsible for the making of the protein or polypeptide which the gene encodes can be detected even within a single cell; similarly, for cells and tissues infected by a virus, the product of a viral infection, the viral RNA, or even the viral DNA itself can be detected within the infected cells or tissues. Such protocols provide enormous amounts of useful diagnostic and/or scientific information because the presence or absence of the specific nucleic acid of interest can be correlated, directly and indirectly, with one or more cells of observable structure and morphology and in this way provide a basis for a clinical diagnosis and/or prognosis.

It is apparent even to the casual reader that the present invention as a whole is heavily dependent upon a thorough knowledge and understanding of recombinant DNA technology and its many applications within molecular biology and clinical/diagnostic situations. The recombinant DNA techniques employed when making and using the present invention are well established and constitute recognized methods for the isolation of specific plasmids; for the use of restriction endonucleases; for ligation of DNA fragments in-vitro; for the preparation of predetermined nucleotides in sequence as hybridization probes; and for the various methods of labelling such DNA (or RNA) probes using a variety of labels such as radionuclides. Accordingly, it is presumed that the reader is familiar with the applications and limits of the various techniques and will recognize that minor changes in reagents, concentrations, temperature, reaction times, and similar alterations of known methods are merely obvious variations of choice. Any major differences from the published and accepted techniques will be identified and described in detail as necessary. However, no description or repetition of the many compositions, protocols, and manipulative techniques will be given here for these well known procedures. For a complete description and recitation of the protocols and for more detailed information regarding recombinant DNA techniques and expression vectors, the reader is directed to the following publications: Maniatis et al., *Molecular Cloning, A Laboratory Manual*, Cold Spring Harbor Laboratory (1982); Davis et al., *Advanced Bacterial Genetics*, Cold Spring Harbor Laboratory (1982); Primrose and Dimmock, *Introduction To Modern Virology*, Second Ed. (1980); and Old and Primrose, *Principles Of Gene Manipulation* (1980), the texts of which are expressly incorporated herein by reference.

In addition it is presumed and understood that the terminology, technical and otherwise, used herein follows their usual, well understood meanings as they are used and applied in common parlance or the technical literature. For these reasons, only if a term has not been used previously within the field generally or if an unusual definition is employed, then and then only will a formal definition be provided as part of the text. For this reason, technical terms such as nucleotide, nucleic acid, plasmid, genome, expression vector, transcription, translation, expression and similar technical terms are presumed to be commonly understood by the practitioner ordinarily skilled within this art.

To fully and properly appreciate the subject matter as a whole which comprises applicants' present invention, one must comprehend that this invention represents a significant improvement and extension of in-situ hybridization by providing greater efficiency of hybridization and detection as well as better biochemical and morphological preservation of samples using a protocol which is much more rapid and simple than any previously existing protocol. The improved methodology is based upon the identification of critical parameters derived via a novel, highly efficient means of quantitating in-situ hybridization results which was systematically applied to an original and clearer definition of the methodological objectives. The objectives as originally defined are intimately related and dependent upon each other and optimize the in-situ hybridization technique. The objectives include all of the following:

1. To maximize the sensitivity of the assay by increasing efficiency of hybridization and detection of specific "signal" and by decreasing non-specific "noise".
2. To maximize the retention of the target nucleic acid sequences in the cell or tissue sample.
3. To maximize preservation of the other biochemical and morphological characteristics of the cell or tissue sample.
4. To minimize both the total time and the number and complexity of technical steps required for the protocol.

Previously known in-situ hybridization and detection techniques have failed to be aware of the critical parameters controlling the method and have failed to properly define the existence and interdependence of their specific objectives. Accordingly, it has been previously impossible to systematically define the factors controlling the accuracy, efficiency, and reproducibility of previously known techniques and it has been equally difficult if not impossible to systematically evaluate the effects of varying one or more factors within any given procedure or system. Applicants' invention thus relies upon two major developments: First, upon the unique recognition and identification of specific factors as being critical parameters; second, upon evaluating and optimizing the critical parameters of fixation protocol, hybridization time, cell pretreatment, probe size, probe concentration and others with respect to all the methodological objectives defined above.

Previous attempts to improve in-situ hybridization methodology depended on single-cell analysis of grains by autoradiographic detection, an approach too laborious to facilitate extensive methodological analysis. The invention described herein was made feasible by adoption of a novel experimental approach for rapidly and objectively quantitating results. Samples with equivalent numbers of cells were hybridized with labeled probes and results obtained immediately by counting radioactive decay in a scintillation counter or by detecting chromogenic enzyme reaction products. The efficiency of this approach allowed analysis of nearly ten thousand samples over a one year period for the evaluation of critical experimental parameters and the interaction between these parameters to a far greater extent than was previously possible.

Some of the salient features and advantages of the present invention which differentiate it from the prior art are as follows:

1. Reduction of time for the hybridization reaction from days to hours or, in some cases, minutes.
2. Reduction of post-hybridization rinses from several hours or days to minutes.
3. Elimination of a number of prehybridization treatments of the cell or tissue sample which were found to be either unnecessary or detrimental to the objectives cited above. The following steps, generally used in the prior art, have been eliminated:
   Incubation in proteinases,
   Incubation in acid,
   Incubation in acetic anhydride,
   Prehybridization,
   Dehydration.
4. Characterization of the nature of the optimal fixative for in-situ hybridization and of the effect the fixative employed has on the other steps in the protocol such as cell pretreatments and probe size.
5. Demonstration that under the fixation conditions specified, probe fragments can be used that are much larger than those considered useful in the prior art, and that the use of these larger probe fragments has potential to provide greatly amplified hybridization signals due to enhanced formation of probe "networks".
6. Definition of an in-situ hybridization protocol that provides preservation of cellular nucleic acid sequences and morphology while achieving reproducible hybridization efficiencies tenfold greater than previously reported for nick-translated DNA probes. This enhanced hybridization efficiency is not dependent upon networking of large probe fragments which can provide even further increases in hybridization.
7. Reduction of the time required to detect the presence or absence of a radioactive probe hybridized in-situ from a period of weeks to only minutes by a novel application of Cerenkov radiation or scintillation counting to yield quantitative information as to the average number of nucleic acids detected per cell. This new methodology provides much of the same information as standard solution or filter hybridizations, but is much more rapid, less laborious and requires markedly smaller cell or tissue sample.
8. Modification of a commercially available technique for the enzymatic detection of biotin-labeled probes on filters such that the method can now be successfully used to detect biotin-labeled probe hybridized within cells. The methodology in the prior art was not applicable to hybridization in-situ because the reagents involved in the enzymatic reaction exhibited a very high degree of non-specific binding to cellular material.
9. A diagnostic kit whose prepared reagents are utilized in the described manner to provide in-situ hybridizations and detection of labeled probes with speed, efficiency, accuracy and without substantial cellular destruction or changes in cell morphology.

To promote ease of understanding and to more fully evaluate the empirical data contained within the experiments which follow herein, the detailed description of the present invention will be divided into distinct parts. These will be identified as follows: the in-situ hybridization method; methods for quantitatively detecting hybridized nucleic acid sequences; the advances of the novel in-situ hybridization method and detection methods in combination; kits utilizing in-situ hybridization methods and detection methods; and the experimental studies which identified the critical parameters, yielded their optimal values, and demonstrated their respective effects.

I. THE IN-SITU HYBRIDIZATION METHOD

The methodology as a whole is best described and most easily illustrated when used in the context of a single model test system. The illustrative purpose of the hybridization methodology described hereinafter is to analyze the presence of a particular messenger RNA for actin protein during skeletal myogenesis using a chicken embryonic cell model system which has been extensively investigated previously and is well defined. Because mRNA presents particular difficulties to the user because of its lability, its solubility and its dispersal throughout the cytoplasm of a single cell, the use of a simple and highly efficient method for the detection of cellular mRNA (and by implication cytoplasmic DNA sequences as well) via assessment of critical parameters demonstrates the utility and the variety of applications for the improved in-situ hybridization method. It will be expressly understood and appreciated, however, that the novel methodology is equally applicable to a wide variety of other systems, cells, and tissues for the hybridization of specific nucleic acids of interest with concommitant preservation of cell integrity and morphology. On this basis, the described empirical experiments involving the chicken embryonic cells and tissues are merely illustrative and representative of the many applications in which the novel hybridization method may be used advantageously.

Cell Cultures and Tissues

A variety of cultured cells were tested to determine the general applicability of the methodology, but the bulk of the work used primary cultures of chicken embryonic muscle which contain fibroblasts as well as myoblasts. The myoblasts differentiate into multinucleated myotubes which then synthesize large amounts of actin as well as other muscle-specific proteins. The results of testing these fibroblasts, myoblasts and myotubes are described within the experimental series which follow herein. In addition, a non-exclusive selection of other cell types in culture were tested for which no empirical data is provided herein. These included a number of mammalian cell lines: the L8 line of rat myoblasts; Chinese hamster ovary cells; a rat pheochromacytoma cell line (PC12); human HeLa cells; NIH 3T3 cells; and squamous cell carcinoma from mice. The novel in-situ hybridization methodology was found to be equally useful and quantitatively accurate for each of these cell types also.

Skeletal myoblasts were isolated from the pectoral muscle of 12-day old chicken embryos and cultured by standard techniques [Paterson and Strohman, Dev. Biol. 29:113-133 (1972)]. These cultures cells were plated at a density of $2 \times 10^6$ in 100 millimeters (hereinafter "mm") plates containing glass coverslips (of approximately 22 mm$^2$ surface area) which had been previously autoclaved in 0.5% gelatin. The culture medium comprised Minimal Essential Medium [Difco catalogue], 10% fetal calf serum, and 2% chick serum. For most experiments in the series, the cells were fixed after three days of incubation at 37° C. in 5% CO$_2$ when 20-30% of the cells had differentiated into multinucleated myofibers. Where indicated, primary fibroblast cultures were used in lieu of muscle cultures and were isolated from whole chicken embryos then cultured under similar conditions.

For those test experiments in which retention of total cellular RNA was monitored, $^3$H uridine commercially obtained as 38.4 Ci/n mol (New England Nuclear Company) was added to cell cultures three hours prior to fixation, at a final concentration of 10 uCi/per milliliter (hereinafter "ml"). The coverslips containing these cells were rinsed twice in Hanks Balanced Salt Solution and fixed using specific fixatives. After being fixed, the individual coverslips were placed in 70% ethanol and stored at 4° C. until required for use.

Fixation of Cells And Tissues

In the model test system, coverslips containing cultured cells or tissue sections are combined with a fixative preferably for 1-15 minutes.

The purpose of fixing cells (and tissues sections) is to preserve the cells (or tissue section) in a morphologically stable state such that the mRNA is retained within the cellular matrix under the rigorous conditions present during in-situ hybridization. However, overextensive insolubilization of the proteins by the fixative within the cellular matrix via cross-linking and/or precipitation renders the cytoplasm of the cell substantially impermeable to all but the smallest sized probes. The preferred fixative is thus one which maintains and preserves the morphological integrity of the cellular matrix and of the nucleic acids within the cell as well as provides the most efficient degree of probe penetration. The preferred method thus utilizes a fixative which is able to preserve and retain the nucleic acids of the cell and concomitantly restricts the cross-linking and/or precipitation (insolubilization) of the proteins in the cellular matrix such that the cell (or tissues) remain substantially in an open configuration for probe penetration and subsequent hybridization. Such a fixative is paraformaldehyde, a solid formaldehyde polymer which can be solubilized by dissolving the solid as a 4% solution in phosphate buffered saline containing 5mM MgCl$_2$. It should be noted, however, that if the paraformaldehyde fixative is allowed to age over a period of a few weeks, the paraformaldehyde breaks down into several substances, at least one of which is destructive to cellular RNA. In contrast, bottled formalin solutions were found to be unpredictable in their RNA retention properties.

In addition, it is only now recognized that other conventionally known and used fixatives are inadequate and/or destructive for cellular RNA retention under conditions identical to those employing paraformaldehyde. A representative list of known fixatives which are less suitable for use with the in-situ hybridization methodology hereof include the following: 4% glutaraldehyde in phosphate buffered saline (hereinafter "PBS") plus 5 mM MgCl$_2$; a fixative comprising three parts ethanol and one part acetic acid; Carnoy's fixative comprising one part acetic acid, six parts ethanol, and three parts chloroform; 1% osmium tetroxide; Bouin's fixative comprising 1.21% picric acid, 11.0% formaldehyde, and 5.6% acetic acid in aqueous solution; Zenker's fixative comprising 5.0% mercuric chloride, 2.5% potassium dichlorate, 5.0% acetic acid, and 1.0% sodium sulfate in aqueous solution; and a fixative comprising 3 parts acetic acid and 1 part methanol.

Avoidance Of Cell And Tissue Pretreatments

When utilizing the novel in-situ hybridization methodology it is preferred that extensive cell or tissue section pretreatments be avoided. In particular, proteolytic cell pretreatments which are highly favored in previously known methodologies are to be explicitly avoided and are not favored for either RNA retention or efficient hybridization. Hence, unless it is critical for the purposes of the individual assay system, the only cell treatments prior to hybridization which should be performed for the fixed cultured cells (or tissue sections) are removal from 70% ethanol and rehydration in a solution comprising 0.1M glycine and 0.2M tris HCl pH 7.4 for about 10 minutes. The coverslips containing the fixed cultured cells (or tissues sections) are then placed in a polar ionizing solvent such as a 50% formamide solution preferably containing 2×SSC buffer (0.3M sodium citrate, pH 7.0) for a period of 5 minutes or longer prior to hybridization of the cells.

It will be recognized and appreciated by practitioners in the art that the avoidance of cell pretreatments in the present invention stands in opposition to and in contradiction of large numbers of prior art protocols for in-situ hybridization which subject the fixed cells to a variety of harsh pretreatments in an overall attempt to increase the efficiency of hybridization by rendering the targeted nucleic acids of interest within the cell more accessible to the probe. [John et al., *Cell* 21:501-508 (1977); Brahiic and Haase, *P.N.A.S. USA* 75:6125-6129 (1978); Angerer et al., *Nucleic Acids Res.* 9:2819-2840 (1981); McAllister et al., *Science* 222:800-808 (1983); Edwards and Wood, *Dev. Biol.* 97:375-390 (1983); Hafen et al., *Embo J.* 2:617-623 (1983); and Gee and Roberts, In *DNA* 2(2):157-163 (1983)]. Most of these prior art methods are directed towards permeabilization of the fixed cellular protein matrix. These methodologies include the use of protease, acid, detergents, and/or heat denaturization. Other known pretreatments which are used to reduce the background signals or noise of the cell include acetylation of the sample with reactants such as acetic anhydride or prehybridization with inhibitors or non-specific competitors of nucleic acids such as non-specific DNA (e.g. salmon sperm), non-specific RNA (e.g. tRNA), polyvinyl pyrrolidone, or Denhardt's solution [Angerer and Angerer, *Nucleic Acid Res.* 9:2819-2840 (1981)]. All of these treatment compositions and the conventional practice of cell pretreatment is preferably avoided as being unnecessary, time consuming, detrimental to RNA retention, and overtly destructive to cellular components and matrices with concomitant dissociation of and loss of integrity for cell morphology and structure.

Preparation of The Probe

The preferred probe is a labeled probe comprising at least one known or predetermined nucleotide sequence and an identifying label such as a radionuclide or biotin moiety. The nucleotide sequence may be substantially similar to at least a portion of the nucleic acids normally present within the fixed cell or tissue or may be substantially similar to a specific nucleic acid of interest which is not normally present within the cell and is associated with an abnormal or pathological state. The probe is a DNA (or RNA) fragment ranging in size from about 20-4000 nucleotides in size. Probe fragments about 4000 nucleotides in length are presently the largest sized probes believed capable of penetrating the cell (or tissue) for in-situ hybridization. Nevertheless, if larger sized probes can be prepared and utilized, these are deemed to be within the scope of the invention. These larger sized probes are advantageous because they are able to provide large increases in signal and allow detection of much smaller numbers of molecules within the cell.

Within the model test system utilizing primary cultures of chicken embryonic muscle cells, the labeled probe comprises DNA sequences derived from the 4.5 kilobase (hereinafter "kb") plasmid pBR322 into which the full-length DNA transcript coding region of chicken beta actin (2 kb) had been inserted at the Pst 1 site [Cleveland et al., *Cell* 20:95-105 (1980)]. The actin DNA sequences were chosen for use in the probe because all the chicken cells tested expressed actin in relative abundance (1,000 copies per cell) and the differentiating muscle system of the chicken embryo results in myotubes which express actin in much higher levels (10,000 copies per nucleus). The control probe used for background counts (noise) were fragments of the pBR322 plasmid without actin DNA or any other insert sequences represented in the cellular RNA of the cells. For preparation of actin probes and control probes, plasmid DNA was nick-translated in the conventional manner using a reactant comprising an identifying label conjugated to a nucleotide such as dCTP [Rigby et al., *J. Mol. Biol.* 113:237-251 (1977)]. All nick-translations utilized endonuclease free DNA polymerase I (Boehringer Mannheim). Subsequently each labeled plasmid was combined with DNAse in quantities varying from 1.0-300.0 ng/ml which yielded a variety of labeled actin probe and control probe fragments respectively of differing nucleotide size.

Two preferred kinds of identifying label were used for the probes: radionuclides and biotin. The preferred radionuclide labels are $^{32}P$, $^{125}I$, $^{35}S$, and $^{3}H$. In addition to these preferred radionuclides, any of the other known and conventionally used radionuclides which can be chemically bonded or enzymatically incorporated into a nucleic acid fragment or nucleotide sequence using either the nick-translation methodology or other suitable methodology may also be used without limitation. Nevertheless, the actin probes and control pBR322 probes are preferably nick-translated with $^{32}P$-dCTP (Amersham) and in which the specific activity of the $^{32}P$ probes range from $0.8-2.2 \times 10^8$ cpm/ug (Cerenkov Counts). Only the $^{32}P$ labeled probe fragments are able to be measured by Cerenkov radiation which provides greater convenience in comparison to scintillation counting procedures.

In general, actin probes and control probes prepared with $^{32}P$ nucleotides are able to incorporate $10^8$ Cerenkov counts per microgram and give an optimal signal corresponding to 200 picograms of probe subsequently hybridized per $10^5$ cells. At this level of specific activity, the background noise of control probes is in the range from 0.5-3.0 picograms yielding a generally reproducible limit for detection in the range of a few picograms per sample. In the alternative, radioactive isotopes of iodine, sulfur, and hydrogen (tritium) are also useful.

Biotin labeled probes are preferably prepared by nick-translating actin probes and control probes using the Rigby et al. methodology and a biotinyl-dUTP reactant containing a 11-atom spacer arm between the 5 position of the pyrimidine ring and the carboxyl group of the biotin moiety (commercially available from ENZO Biochemical Co.). Use of the 11-atom spacer arm rather than shorter length spacer arms is said to improve the ability of the biotin to react [Singer and Ward, *Proc. Natl. Acad. Sci. USA* 79:7331–7335 (1982); Langer et al., *Proc. Natl. Acad. Sci. USA* 78:6633–6637 (1981)].

It will be recognized that other identifying labels may also be used with the described probes. These include fluorescent compositions, as well as conjugated proteins, enzymes, or antibodies and antigens. All of these are deemed useful and within the scope of the present invention.

Probe Size Effects

The penetrability of the labeled probes into fixed cells and tissues and the efficiency of the hybridization with the mRNA sequences within the cellular matrix is directly influenced by the size of labeled probe fragments after nick-translation. A variety of different sized probes are obtained by varying the amount of DNase in the nick-translation reaction from 1.0 ng/ml to 300 ng/ml such that the lowest concentration yields fragments with a mass average molecular size of 2000 nucleotides and the greatest concentration yields fragments averaging 100 nucleotides in length. Actin probe fragments and control probe fragments were isolated and determined for size by 1.5% alkaline agarose gel electrophoresis using appropriate molecular weight markers [Boehringer Mannheim Biochemical Co.]. With paraformaldehyde fixed cells and tissues, a broad range of probe fragment sizes ranging from about 20 to more than 2000 nucleotides were found to be useful and acceptable. The preferred size of probe, however, will vary with the application and the nature of the identifying label. For quantitative results using radionuclide labels, the preferred size is in the range of about 200–500 nucleotides and the optimum total concentration of probe is used at the saturating level of 20 ng per 10 ul of reaction medium (2 ug/ml). For purely qualitative data using radiolabeled probes, the preferred probe size is at least 1500 nucleotides and most preferably is greater than 2000 nucleotides in size. With biotinylated probes, the probe fragments should be smaller than the corresponding radiolabeled probe; accordingly these are preferably less than 200 nucleotides in length and are most preferably about 100 nucleotides in size.

Under normal use conditions, it is not absolutely required that labeled fragments be of a limited size or range uniformly. Rather, the actin DNA containing plasmid and the control pBR322 plasmid respectively may be individually combined with varying quantities of DNAse to yield a mixture of differently sized fragments ranging from 100 to more than 2000 nucleotides and each mixture of differently sized fragments may be used at varying nucleic acid concentrations ranging from 0.2–20.0 ug/ml as desired. It is therefore envisioned and expected that fluid mixtures of varying probe size will be used as a common practice.

Use of fragments sizes in the range of 1500 nucleotides and greater promotes probe networking, a situation in which unusually high signals are obtained. A commonly accepted definition of probe networking is the formation of a complex of DNA molecules by interstrand hybridization [Wahl et al., *P.N.A.S. USA* 76:3683–3687 (1979)]. As described herein under "Probe Networks", these unusually high signals are due to the presence of "junction pieces" containing both actin and pBR322 DNA sequences which hybridize with cellular mRNA and create an amplification of probe signal by reannealment at the mRNA target site. This unusually high and improved signal with large sized probe fragments is not reproducible in a regular manner and the extent of signal enhancement varies greatly from sample to sample. For this reason, it is preferred that probes 1500 nucleotides or more in size be used only for qualitative assays where high sensitivity is required and that probe fragment sizes of less than 1500 nucleotides and most preferably less than 500 nucleotides in length be used when reproducible, quantitative analyses are to be performed.

In addition, it has been found that when using fragment lengths greater than 2,000 nucleotides as probes, there is a higher background count (noise) as measured by scintillation counting whereas such background counts (noise) become relatively low for probe sizes below 1500 nucleotides. It is noted, however, that should probe size lengths greater than 2,000 nucleotides be desired for use, the very high background noise can be effectively reduced up to 80–90% by pretreatment of fixed cells (or tissues) with acetic anhydride. In such instances, prior to hybridization, the fixed cells (or tissues) are to be immersed for ten minutes in freshly prepared 0.25% acetic anhydride in triethanolamine buffer, pH 8.0 at room temperature [Angerer et al., *Nucleic Acids Res.* 9:2819–2840 (1981); Hayashi et al., *J. Histochem. Cytochem.* 26:677–679 (1978)].

It should be noted also that all of the foregoing discussion regarding the length of the probe fragment is directed to radionuclide labeled probes exclusively. The situation concerning biotin labelled probes is rather different. Both the efficiency of hybridization and the background noise (signal) resulting from use of biotin labeled probes are directly dependent upon the size of the probe. It is therefore useful to limit the fragment size of biotinated probes to approximately 200 nucleotides or less in order to avoid non-specific binding and to obtain quantitative results with signal to noise ratios from 10:1 to 50:1.

Moreover, one can synthesize single strand fragments of DNA 20–25 nucleotides in length which are complementary for a specific sequence of messenger RNA [DNA Synthesizer from Applied Biosystems]. These single-stranded pieces can be used as labeled probes to detect cytoplasmic nucleic acids of interest in cells with an efficiency of hybridization twice as high as with nick-translated double stranded probes (detection being more difficult). Biotinated dUTP can be added to the ends of these molecules with terminal transferase enzymes [Bio-note 202 from Enzo Biochemical Co.]. Phosphorus-32 can also be added by the use of kinasing enzyme [Maniatas, Cloning Manual]. The means of their detection is as described herein.

The use of such synthetic, single stranded DNA as labeled probes is deemed to be commercially significant because the DNA can be manufactured synthetically in large quantities at low cost; and the probe penetration is better because the DNA is single-stranded and small.

The Hybridization Fluid

The composition of the hybridization fluid is a mixture of components which optimize the conditions of in-situ hybridization. It will be understood that individual hybridization fluid mixtures are prepared comprising the actin probe fragments and the control probe fragments respectively. The quantity of total probe used is a predetermined amount which should exceed the estimated amount of available RNA believed to be within the sample about 100:1 in order to drive the hybridization reaction efficiently and to promote a high rate of probe:RNA annealing. In quantitative terms, this requires that a range of probe concentration ranging from 0.2 ug/ml (2 ng/10 ul reaction fluid)–20.0 ug/ml (200 ng/10 ul reaction fluid) be used with a saturating probe concentration of 2.0 ug/ml (20 mg/10 ul reaction fluid) being most optimal to give reliable signals 70 fold above background.

A preferred hybridization fluid thus comprises the following: 2.0 ug/ml of actin probe or control probe respectively; non-specific competitors of the probe comprising 5.0 ug sonicated salmon sperm DNA (commercially available from Sigma Corporation) and 20 ug *E. coli* transfer RNA (commercially available from Boehringer Company) as an initial mixture which was then suspended in 5.0 ul of an ionizing solvent such as 100% formamide and heated to 70°–80° C. for approximately 10 minutes. After being heated, the DNA in formamide solvent was combined with an equal volume of hybridization buffer, a fluid mixture composed of 4×SSC (0.6M sodium citrate) buffer, 2.0% bovine serum albumin, 20 mM vanadyl sulfate [Berger and Birkenmeier, *Biochemistry* 18:5143–5149 (1979)], and 20% dextran sulfate (commercially available from Sigma Corporation). The final concentration of the completely prepared hybridization fluid thus comprises 50% formamide, 2×SSC buffer (0.3M sodium citrate), 1% bovine serum albumin, 10 mM vanadyl sulfate, and 10% dextran sulfate. The preferred polar ionizing solvent, formamide, used in this fluid was routinely obtained from commercial sources and was preferably deionized using AG-501-8X analytical mixed bed resin (Biorad Corporation) for 30 minutes before use.

The In-Situ Hybridization

One of the major advantages of the novel in-situ hybridization method is that relatively small numbers of cells comprise a sample and large numbers of identical samples may be tested over a very short period of time. From each isolation of cultured cells, large numbers of coverslips ranging from 60–100 in number with each coverslip containing up to $10^6$ cells of uniform density were utilized so that the individual test samples within and between different experiments could be directly compared and statistically evaluated. Preferably, just prior to the hybridization step, each coverslip containing the cultured cells is cut in half using a diamond pencil to yield two identical test samples. One half of each coverslip is then hybridized using a hybridization fluid comprising labeled actin probe while the other half coverslip is hybridized using a fluid comprising a labeled control probe (the pBR322 DNA nucleic acid sequences lacking the actin insert). For comparison purposes only, an additional two coverslips from each cell type and preparation are stained with the DNA fluorochrome 4'-6-diamidino-2-phenylindol (hereinafter "DAPI") at a concentration of 1.0 ug/ml at room temperature for ten minutes. These stained coverslips are then viewed using a Zeiss ICM microscope with epifluorescence optics for determination of cell numbers and percent of nuclei in multinucleated myotube preparations. In addition, when required, the total RNA is isolated from coverslip with 0.5% Triton X-100 and subsequent phenol extraction using the method of Singer and Kessler-Ickeson [*Eur. J. Bioch.* 88:395–407 (1978)] and subsequently quantified by measurement of its optical density at 260 nanometers.

Each half coverslip represents one test sample which is preferably placed cell side down onto a drop containing 10.0 ul of the appropriate hybridization fluid supported by a parafilm sheet. Care should be taken that the hybridization fluid is applied immediately after its preparation while it is still relatively warm to each sample under test. Each sample is then covered loosely with another sheet of parafilm and incubated at 37° C. in a 100% humidified chamber for a period of time ranging from not less than 10 minutes and not more than 24 hours in duration.

It will be appreciated that prior in-situ hybridization techniques require a hybridization time ranging from not less than one day and as much as four days in duration. In contrast, the present invention provides results that are detectable in about 10 minutes hybridization time; offers quantitative data which is reproducible at 30 minutes duration and is complete within the first 3–4 hours. It should be noted, however, that hybridization should not exceed approximately 24 hours in duration because the degree of hybridization within the sample may decrease by 50% and more if the samples are incubated longer than 24 hours in the hybridization fluid. It is preferred that the incubation period be not longer than approximately three or four hours in duration; but if this is not feasible or desirable to the user, the time may be extended up to 24 hours or conversely decreased to 30 minutes without detrimental loss of either hybridization efficiency or quantitative accuracy.

Post Hybridization Rinses

After completion of the hybridization, each sample (half coverslip) is preferably placed in a 10 ml volume Coplin staining jar (commercially available from VWR) or a Petri dish and rinsed three times using three different rinses for preferably 30 minutes duration each. The rinsing solutions to be used serratim are: a first rinse comprising 2×SSC buffer (0.3M sodium chloride and 0.03M sodium citrate) and 50% formamide at 37° C.; a second rinse comprising a mixture of 1×SSC buffer (0.15M sodium chloride and 0.015M sodium citrate) and 50% formamide at 37° C.; and a third rinse comprising 1×SSC buffer at room temperature on a shaker. More harsh rinse solutions and more extensive rinsing periods were found to be unnecessary. After this three rinse cycle, each sample is ready immediately for quantitative or qualitative detection of the in-situ hybridization.

In addition, the rinsing times may be decreased to 5 minutes duration each with little loss of effectiveness. It will be recognized that such short rinsing periods are contrary to generally accepted practices; most previously known techniques require extensive rinse procedures lasting as long as several days in duration and using as much as several liters of rinse solution per sample. Insofar as is presently known, the novel methodology is the first to utilize rapid and minimal rinsing of samples based upon optimal rinse conditions.

The unique in-situ hybridization methodology described above and the experimental data provided hereinafter demonstrate the major advantages which overcome the defects and deficiencies of previously known hybridization techniques. In short, the defects of long and tedious assays, non-reproducible and non-quantitative results, and poor detection have been eliminated. It should be especially noted that not only have the simplicity and speed of the hybridization been increased, but also the efficiency of the hybridization has been increased up to ten fold over prior art practices with concomittant increases in sensitivity.

II. METHODS FOR DETECTING IN-SITU HYBRIDIZED CELLS

Isotopic Detection Of Radiolabeled Probes

The preferred novel methodology for detecting a radiolabeled probe, whether or not it was hybridized with a sample in accordance with the earlier described novel and improved in-situ hybridization methodology, employs well known scintillation counting equipment and the respective techniques of counting radioactive decay by Cerenkov radiation and scintillation counting. As is understood by practitioners ordinarily skilled in this art, Cerenkov counts are limited to use of $^{32}P$ labeled probes in aqueous solution whereas scintillation counting employs a scintillation fluid containing primary and secondary scintillators in toluene as a carrying medium and is thus more suitable for use with sulfonated, and tritium labeled probes. Scintillation fluid is a requirement for nuclides of low beta energy so that the short track of the beta particle will encounter a chemical dissolved in solution which will emit light at the time of collision. Lower energy emissions of nuclides such as $^3H$ and $^{35}S$ require the presence of this chemical. $^{32}P$ emits a high energy particle which interacts with water via the speed of the particle such that light is emitted; this emitted light can be counted by the photometer in a scintillation counter directly.

It should be recognized that, insofar as is presently known, the use of a scintillation counter to quantify in-situ hybridization results, based either on Cerenkov radiation or scintillants, is a completely juxtaposition of these methodologies which dramatically increases the efficiency and quantifiability of the in-situ hybridization technique and greatly extends the types of applications for which the technique will be useful. The novelty of the invention is best evidenced by the total absence within the prior art in-situ hybridization literature of any instance in which hybridization of nucleic acids in-situ was ever quantified using Cerenkov radiation or scintillation counting. Traditionally, in-situ hybridization has always been thought of and applied as a technique for the single cell analysis of nucleic acids and never as a method for rapidly obtaining quantitative information about the average number of copies of DNA of RNA per cell in a population of cells. The juxtaposition of the in-situ hybridization method with the scintillation counting method thus provides a rapid and simple alternative to the conventional solution or filter hybridization techniques which require far greater numbers of cell or tissue samples.

For quantitation of $^{32}P$ labeled probes, each hybridized test and control sample of cells (or tissues) is placed in 3 ml of PBS in scintillation vials, cell side up, and the Cerenkov radiation (counts) immediately obtained for test and control samples using a Beckman LS 9800 scintillation counter in the conventional manner. For other radiolabeled probes and test samples, each control or test sample is first dehydrated with an excess of 100% ethanol for a minimum of 5 minutes. Each dehydrated sample is then air dried for a few minutes, placed in a scintillation fluid such as 2 ml of liquifluor (commercially available from New England Nuclear Company) and then measured for radioactive decay by scintillation counting. In each instance, the quantitative difference in radiation counts, regardless of type, between control samples and test samples provides a quantitative as well as qualitative result in accordance with the specificity of the probe.

The sensitivity limits for the scintillation counting detection method using radiolabeled probes compares well with the known and established method of autoradiography. Autoradiography allows one to obtain quantitative information on single cells by counting the silver grains produced on a photographic emulsion as a result of the radioactive decay [Rogers, A. W., *Techniques of Autoradiography*, 3rd edition, Elsevier Biomedical Press, New York, 1979]. Autoradiography demonstrates that a two month exposure of hybridized samples using a tritiated probe having a specific activity of $2 \times 10^7$ cpm/ug allows detection of 1,000 copies of actin nucleic acid per fibroblast or myoblast with a signal:noise ratio (determined as grains per cell using the actin probe compared to grains per cell using the control probe) of 60:1. This data correlates closely with the results obtained using $^{32}P$ labeled probes and the Cerenkov radiation counting procedure described above. By these results, it is determined that the sensitivity limit of the Cerenkov radiation detection methodology is approximately 17 molecules or copies of targeted nucleic acids per cell. This sensitivity limit is calculated by dividing the empirically obtained signal:noise ratio into the number of copies detected per cell based on a comparison between the results of radiation counting and the autoradiography method. It is also based on the presumption that the radionuclide detection methodology described herein is able to detect a signal:noise ratio of 2:1 with reasonable accuracy.

It is noted further that the scintillation counting method for detecting sulfonated, tritiated, and iodinated probes is equivalent in sensitivity and is directly dependent upon the activity of the nuclide which is measured in counts per minute per microgram of DNA. For $^{35}S$ and $^{125}I$ nuclides, the activities are approximately the same as for $^{32}P$; in comparison $^3H$ is somewhat less sensitive because of its lower decay energy and counting efficiency.

Non-Isotopic Detection Using a Biotin Label

Reagents are commercially available for the enzymatic detection of biotin labeled probes extracellularly on filters using reagents comprising avidin or streptavidin, an enzyme such as alkaline phosphatase which has ben biotinylated and a chromogenic enzymatic substrate [Vectastain ABC kits, DNA detection kits from BRL Laboratories, ENZO Biochemical Co.]. However, attempts to employ these reagents in accordance with the prescribed protocols for detection of labeled probes with in-situ hybridized cells (or tissues) were unsuccessful due to the consistent occurrence of false positives. Control samples which had not been hybridized exhibited approximately the same extent of enzymatic reaction product as did samples which were hybridized in-situ with a biotinated probe, a result found to be caused by non-specific adherence of the reagents to the cytoplasm of the cell under the test conditions employed. Experiments using $^{125}I$ - avidin demonstrated that this reagent was especially adherent to cell cytoplasm when applied in the solution(s) prescribed by the commercial kits (0.1M Tris-HCl, pH 7.5; 0.1M NaCl; 2 mM $MgCl_2$; 0.05% Triton X-100). It is possible, however, to decrease the non-specific binding of larger sized (greater than 200 nucleotides) biotinated probes by 80-90% via a post fixation treatment of the sample using 0.25% acetic anhydride and/or a combination of 0.5% Triton X-100 and 1.0 mM biotin in PBS.

The novel detection method is a modification of prior art protocols for enzymatic detection of biotinated probes which now permits the user to reproducibly detect biotinated probes hybridized in-situ. The improvement comprises using a aqueous salt solution of at least 0.4M concentration as a fluid carrier for the avidin or streptavidin. Empirical testing demonstrates that if avidin or streptavidin is applied in the preferred aqueous 4×SSC buffer (0.6M sodium chloride, 0.06M sodium citrate, 0.05% Triton X-100), non-specific binding of this component to the cells is eliminated. The protocol given below is thus directly suitable for detection of biotinated probes within cells and tissues hybridized in-situ.

The preferred protocol for the non-isotopic detection method is as follows:

1. Preheat Buffer A to 42° C. for a predetermined time. Buffer A comprises 3% w/v Bovine serum albumin (BSA) in 0.1M Tris-HCl, pH 7.5; 0.1M NaCl; 2 mM MgCl$_2$; and 0.05% Triton X-100.

2. Incubate each sample in an excess of preheated Buffer A for 20 minutes at 42° C.

3. Remove Buffer A by blotting each sample on filter paper.

4. Prepare a 2 ug/ml solution of streptavidin or avidin using 1.0 ml of 4×SSC buffer and allow this mixture to stand at room temperature for approximately 10 minutes.

5. Wash each sample once in 2 ml of 4×SSC buffer containing 3% BSA and then twice in 4×SSC buffer without BSA.

6. Incubate each washed sample individually with 1 ug/ml polyalkaline phosphatase prepared in Buffer B for 10 minutes at room temperature. Buffer B comprises 0.1M Tris-HCl, pH 7.5; 0.1M NaCl; 2.0 mM MgCl$_2$; and 0.05% Triton X-100.

7. Wash each sample twice for five minutes with Buffer B at room temperature.

8. Quickly rinse each sample with excess Buffer C. Buffer C comprises 0.1M Tris-HCl, pH 9.5; 0.1M NaCl; 50 mM MgCl$_2$.

9. Combine 33 ul of nitro blue tetrazolium (75 mg/ml in 70% dimethylformamide) with 7.5 ml of Buffer C taking care to keep this mixture protected from light; then vortex the mixture and add 25 ul of bromo-chloro-indolyl phosphate (50 mg/ml in dimethylformamide); vortex and place this prepared solution on each cell sample.

10. Incubate each sample in the dark with gentle shaking at room temperature for a period ranging from 1-24 hours.

III. THE IN-SITU HYBRIDIZATION METHOD AND DETECTION METHODS IN COMBINATION

It is intended and expected that the novel in-situ hybridization method be utilized with one or more of the novel detection methods described herein. Although each may be used separately to advantage, it is when these methodologies are performed in unison that the most desired technical advances provided by the present invention become apparent. These advances are: simplicity, speed, and sensitivity.

Simplicity is provided by eliminating the number of steps and reducing the complexity of the steps required to perform the respective methods; speed is provided by the use of but a few reagents for shorter times and commonplace instrumentation which does not require either skilled technician or extensive handling; sensitivity is provided by the ability to detect most of the targeted mRNA (or DNA) in the sample rather than only a minor fraction of the targeted nucleic acids of interest in the cells or tissue. The best evidence of both these advances is demonstrated by the Minimal Time Protocol which follows.

Summary of a Minimal Time Protocol

The following is an outline of the technical steps in the novel method indicating a minimal time for each step, beginning with previously prepared solutions and reagents.

| Minimal Time | | Manipulation |
|---|---|---|
| 5 min. | 1. | Fixation of cell or tissue sample in appropriate fixative such as 4% paraformaldehyde for 5-15 minutes. If required, samples may be stored at 4° C. in PBS for two weeks or in 70% ETOH indefinitely. |
| 5 min. | 2. | Rehydration of sample in 0.2 M Tris .01 M Glycine for five minutes. |
| 5 min. | 3. | Incubation in 50% formamide, 2 × SCC buffer for five minutes. |
| | 4. | While the samples are incubating, heat 5 ul of Solution A per sample to 70-80° C. for ten minutes. Solution A contains 20 ng labeled probe DNA, 15 ug sonicated non-specific competitor DNA, 60 ug non-specific competitor tRNA in 5 ul formamide. Then add 5 ul of Solution B. Solution B contains 4 × SSC buffer, 2% BSA, 20 mM vanadyl sulfate, 20% dextran sulfate. |
| 10 min. | 5. | Hybridization at 37° C. for at least 10 minutes but preferably not more than 24 hours. |
| 15 min. | 6. | Rinse vigorously three times for five minutes each in 10 ml volumes of Solutions C, D and E in succession: Solution C contains: 2 × SSC buffer, 50% formamide at 37° C.; Solution D contains: 1 × SSC buffer, 50% formamide at 37° C.; Solution E contains: 1 × SSC buffer on a shaker at room temperature. |
| | 7. | Detection of hybridization: |
| 2 min. | | A. Radioactive probes ($^{32}$P): place in PBS in vial and read immediately in scintillation counter. |
| 1 hour | | B. Biotinated probes: enzymatic detection with alkaline phosphatase or horseradish peroxides conjugated to avidin. |
| Total Minimum Time For In-Situ Hybridization And Detection | | |

| Radioactive Probe | Biotinated Probe Enzymatic Detection |
|---|---|
| 42 minutes | 100 minutes |

It will be appreciated by persons working routinely in testing laboratories and in research centers that the Minimal Time Protocol may be utilized for tens or hundreds of samples at one time using one or more labeled probes (each having a different nucleotide sequence) and that the entirety of the protocol utilizing multiple samples and multiple probes may be repeated cyclically many times in the course of 8 hours time. In this manner, many hundreds of test samples may be received, tested, and evaluated by relatively unskilled persons within the confines of a single work day.

IV. KITS UTILIZING THE UNIQUE IN-SITU HYBRIDIZATION AND DETECTION METHOD

It will be recognized by practitioners ordinarily skilled within this art that the novel in-situ hybridization protocol described earlier herein is compatible with all previously known methods of detection as well as the novel detection methods described herein. The in-situ hybridization methodology is streamlined so that fewer manipulations are necessary and that these steps may be performed in a much shorter period of time than has been previously possible. It is expected that the reagents will be provided in kit form to practice the protocol which has been optimized for simplicity and for compatibility with a wide variety of detection methods. It is also expected that such prepared kits, containing specifically prepared reagents and probes, will be most applicable in clinical/diagnostic laboratory where the ability to detect the presence (or absence) of specific nucleic acids would serve to positively or negatively identify cancerous or tumor cells, virally infected cells and other pathological states characterized by the presence of specific genes.

How the kit could be used for diagnostic purposes is illustrated by the following example. The diagnosis of whether or not cells taken from a subject are cancerous depends on a pathological evaluation which, in turn, depends on identifying criteria involving cellular morphological parameters, staining characteristics, and the presence (or absence) of certain enzymes and/or surface antigens. Current methods of diagnosis are thus not entirely accurate and are imprecise as to the future prognosis of the cell or tissues. However, the major drawback to diagnostic procedures presently in use is their inability to detect the cancerous nature of the cell or tissues until a tumor has developed on a multicellular level or in gross. Recently it has been demonstrated [U.S. Pat. No. 4,535,058] that the oncogenic potential (the uncontrolled growth) of cells and tissues is the result of a mutated gene known as an "oncogene". The DNA from this gene has been isolated and sequenced to show that it is, in fact, a true mutation of the normal gene, the proto-oncogene. This oncogene has been shown to be present and active in several kinds of human tumors including lung, bladder, brain and the like. The in-situ hybridization of oncogenes as probes specific for a cancerous cell will allow an identification of the mutation in the cells or tissues of a person and a positive diagnosis long before it could be detected pathologically; moreover, in-situ hybridization would indicate the exact type and nature of oncogene mutation being expressed, there being many known oncogenes. The results of the in-situ hybridization would have prognostic value in that it would permit prediction of the growth potential of these now identified cells once the oncogene expressed within the test sample is correlated with known carcinogenic potential. In addition, after the laboratory diagnosis is made, the efficacy of certain regimens of chemotherapy or radiation treatments can be assessed by determining the extent of repression of the identified oncogene(s) after therapy by again utilizing kits for in-situ hybridization of the treated cells. Test kits for in-situ hybridization should preferably be compatible with a hospital pathology laboratory in practice, in equipment, and in the skills demanded from the user. Such kits, being simple, accurate and rapid, are then expected to become an integral part of the routine testing procedures used by the laboratory. Each such kit would then be formulated to identify and detect a particular condition. Some examples are the detection of genital herpes in cells from cervical smears or AIDS virus from peripheral blood cells. The present invention has empirically detected the presence of AIDS (HTLV-III) virus in infected human lymphocytes and empirically detected the presence of herpes virus in tissue sections taken from the autopsied brain of patients who suffered from central nervous system disorders (e.g. brain tumors and Alzheimer's disease).

Kit Contents

Preferred Reagents For In-Situ Hybridization

Solution A: formamide (deionized); dextran sulfate (10%); E. Coli DNA (100 ug/ml); tRNA (100 ug/ml); and vanadyl sulfate (10 uM).

Solution B: 4×SSC buffer [0.6M sodium chloride and 0.06M sodium citrate, pH 7.2].

Solution C: 4% paraformaldehyde in phosphate buffered saline containing 10 mM magnesium chloride.

Probes: (dry preparations in preset quantities within microcentrifuge tubes);

Probe A: positive control DNA with an identifying label;

Probe B: a test probe comprising an identifying label and at least one nucleotide sequence substantially similar to at least a portion of the specific nucleic acid of interest suspected of being present in the sample;

Probe C: negative control DNA with an identifying label.

The nature of the identifying label will vary with the intended method of detection.

Preferred Reagents For Detection Of Hybridized Probes

For radionuclide labeled probes:

$^{32}P$ labels: any physiological aqueous solution.

$^{35}S$ and $^{3}H$ labels: a medium (e.g. toluene) containing primary and secondary scintillators (e.g. PPO). Use of commercially available scintillation counting fluid such as liquifluor (New England Nuclear Co.) is most convenient.

For biotinylated probes 2 sets of standard reagents may be used:

Set I

Solution 1: avidin (2 ug/ml) or streptavidin (2 ug/ml) in 4×SSC buffer;

Solution 2: biotinylated polyalkaline phosphatase (1 ug/ml);

Solution 3: bromochloroindolyl phosphate (50 mg/ml) in dimethylformamide;

Solution 4: nitroblue tetrazolium (75 mg/ml in 70% dimethylformamide).

Set II

Solution 1: avidin (2 ug/ml) or streptavidin (2 ug/ml) in 4×SSC buffer;

Solution 2: biotinylated horseradish peroxidase (1 ug/ml);

Solution 3: hydrogen peroxide (0.03%);

Solution 4: diaminobenzidene (1 ug/ml in 0.1M Tris buffer, pH 7.2).

Each kit will contain a set of instructions which employ these reagents as part of the novel in-situ hybridization method and at least one detection method.

It is expressly understood also that other methods for detecting nucleic acids presently known and used in this art may be prepared as reagents and utilized in kit form with the present invention. These known detection methods include fluorescent detection methods and reagents; autoradiographic emulsions and detection methods; and immunochemical reagents (antibodies and antigens) and immunological detection methods.

V. EMPIRICAL SUPPORT AND DATA

In order to fully appreciate the novel and unexpected manipulative steps comprising the present invention and to demonstrate the effect of varying the critical parameters which control the efficacy of the methodology as a whole, the following experimental studies are presented and summarized in detail. It is expressly understood, however, that the data presented are merely illustrative of the parameters identified and indicates the empirical technique used to identify optimal conditions. Moreover, although all the data presented relates solely to cells, equivalent studies and data have been obtained for tissues; such data has not been included here in order to enhance understanding and clarity. It is also appreciated and understood by the reader that the optimal conditions desired herein may be varied in considerable degree to satisfy the needs or desires of the user and that none of the empirical data presented is limiting or restricting of the invention as a whole per se.

Experimental Series 1: Fixation

The ideal fixative for hybridization to RNA in-situ is one which not only preserves cellular RNA and morphology but does so in such a way that diffusion of the probe throughout the cytoplasmic matrix is maximized. Eight fixatives were evaluated: 4% paraformaldehyde [Singer and Ward, PNAS USA 79:7331–7335 (1982)]; ethanol:acetic acid [Haase et al., W. Virology 119:399–410 (1982)]; glutaraldehyde [Goddard, C. M., Histochemistry 77:123–131 (1983)]; and Carnoy's fixative comprising one part acetic acid:six parts ethanol:three parts chloroform [Enzo Biochemical Company, Protocols for Bioprobe] and the standard pathology laboratory fixatives of Zenker's, Bouin's, and formalin. Representative values of signal, noise, and RNA retention comparative to paraformaldehyde are given in Table 1.

TABLE 1

Signal to Noise Ratios and RNA Retention with Different Fixatives (percent relative to paraformaldehyde as a standard)

|  | Signal (%) | Noise | RNA Retention |
|---|---|---|---|
| Paraformaldehyde | 100 | 100 | 100 |
| (4%) | | | |
| Glutaraldehyde | 34 | 130 | 100–120 |
| (4%) | | | |
| Buffered Formalin (4%) | 45 | 100 | 46 |
| Zenker's | 100 | 600 | 110 |
| Bouin's | 60 | 100 | 77 |
| Osmium Tetroxide (1%) | 45 | 50 | 61 |
| Acetic Acid:Methanol (3:1) | 32 | 100 | 38 |
| Carnoy's | 40 | 100 | 33 |

Coverslips comprising fibroblasts and myoblasts were fixed for times ranging from 1–15 minutes and then hybridized in-situ as described earlier herein for 16 hours. The results provided are the average of two experiments, each of which use triplicate samples. In order to monitor preservation of total RNA, cultures were incubated with $^3$H-uridine immediately prior to fixation The extent of hybridization was evaluated using $^{32}$P label pBR322 actin probe, whereas non-specific "background noise" was quantitatively assessed using $^{32}$P-label pBR322 nucleotide sequences lacking the actin nucleic acid insert.

The results of each of these analyses are presented in FIG. 1, the bars indicating the standard deviations from the average. The $^3$H uridine results on the paraformaldehyde-fixed samples demonstrate that RNA retention remains essentially constant with increasing fixation times ranging between 1–15 minutes. Although there is some variability in the extent of hybridization using $^{32}$P labeled actin probes (using Cerenkov radiation counts), there is no consistent or significant difference between the samples fixed for different times Thus, a treatment as brief as one minute's duration in paraformaldehyde is adequate for both RNA preservation and for hybridization. The 4% paraformaldehyde fixative thus preserves and retains the nucleic acids of the cellular matrix and cross-links and/or precipitates (insolubilizes) the proteins to a limited extent such that the cell remains substantially in a condition for penetration of the actin and control probes.

In comparison, as demonstrated by Table 1 above, the results for samples fixed in a mixture of ethanol and acetic acid (3:1), glutaraldehyde, or Carnoy's fixative are all dramatically inferior to results obtained for paraformaldehyde fixed cells. Use of either the ethanol:acetic acid fixative or Carnoy's fixative results in a loss of 75% or more of the total cellular RNA. Hybridization in-situ is also dramatically reduced to approximately the same degree. Subsequent microscopic observation of these fixed cells verifies and confirms that they do not appear to be well preserved morphologically.

The decrease in cellular RNA in those samples fixed with ethanol/acetic acid mixture or Carnoy's fixative was not due to loss of cells from the coverslips since good cellular retention was obtained with all the fixative protocols tested. Although the ethanol/acetic acid fixative is the most commonly used in this field, our results indicate that it is not the most suitable for use within in-situ hybridization for preservation of cellular RNA. The results using samples fixed in 4% glutaraldehyde also reveal a striking diminution in signal (counts above background) relative to paraformaldehyde fixed cells with the degree of hybridization being reduced by 60-70% in glutaraldehyde fixed cells. The results indicate that not only is the degree and efficacy of hybridization of the actin probe markedly reduced, but the background noise of the pBR322 control was found to be constantly elevated (in some experiments as much as three-fold higher) in comparison to the paraformaldehyde fixed cells. The signal:noise ratio for glutaraldehyde fixed cells is approximately 10:1 as contrasted with a ratio of up to 70:1 for paraformaldehyde fixed cells under identical experimental conditions. This lower signal, however, is not due to a loss of total cellular RNA as is the case using ethanol/acetic acid fixatives and Carnoy's fixative. The data indicates rather that glutaraldehyde preserves RNA to the same extent as does paraformaldehyde. However, the reduced signal and increased background noise observed with glutaraldehyde fixed cells are consistent with the view that the proteins in the cellular matrix have been overextensively insolubilized by the glutaraldehyde; a condition which greatly impedes penetration of the probe and hinders effective rinsing away of non-specific binding. These results demonstrate that one of the primary advantages of paraformaldehyde is that it fixes the cellular matrix in a more open configuration and thus renders the cellular RNA more accessible to probes of various sizes without the need for cellular proteolysis or other drastic pretreatment of fixed cells prior to hybridization. It will be noted that the experiments described hereinafter involving proteinase digestion of fixed cells corroborate and support this view.

Experimental Series 2: Proteolytic Cell Pretreatment

A standard requisite part of almost all previously known and published in-situ hybridization procedures has been the use of post-fixation treatments of cells (or tissue sections) with proteinase [Brigati et al., *Virology* 126:3250 1983); Gee and Roberts, *DNA* 2, pages 157-163 (1983)]. The commonly accepted rationale for employing such proteolytic pretreatment is that partial removal of proteins would allow greater penetration of the probe through the internal cellular matrix and provide greater accessiblity of mRNA for hybridization. The necessity for and the effects of proteinase treatments were examined using varying treatment times and a standard concentration of 5.0 ug/ml proteinase K. Samples comprising myoblasts were incubated for times varying from 10-30 minutes with 5.0 ug/ml proteinase K in PBS containing 5 mM $MgCl_2$ prior to hybridization. Subsequently, hybridization was conducted as described earlier in the preferred embodiments. The results are presented within FIG. 2 and represent the average of two experiments, each of which utilize duplicate samples.

Figure 2A:
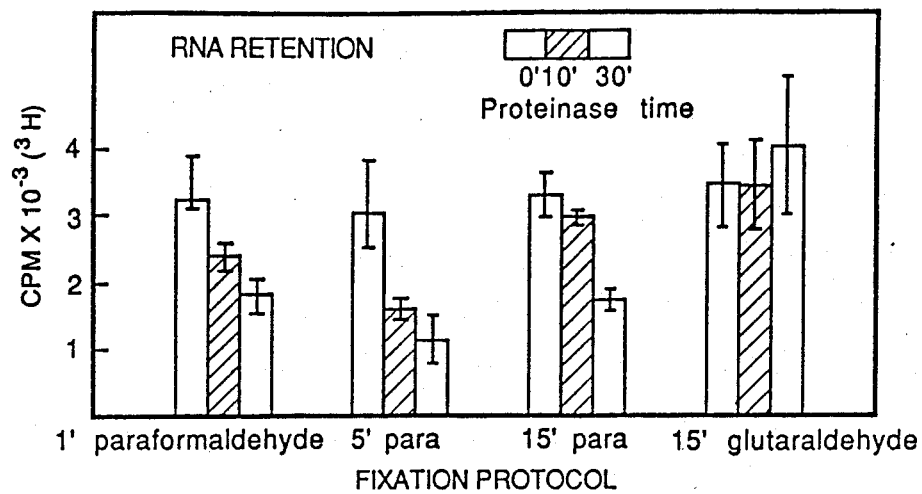
FIGS. 2A and 2B are individual graphs illustrating the effect of proteinase digestion on hybridization and RNA retention.
Figure 2B:
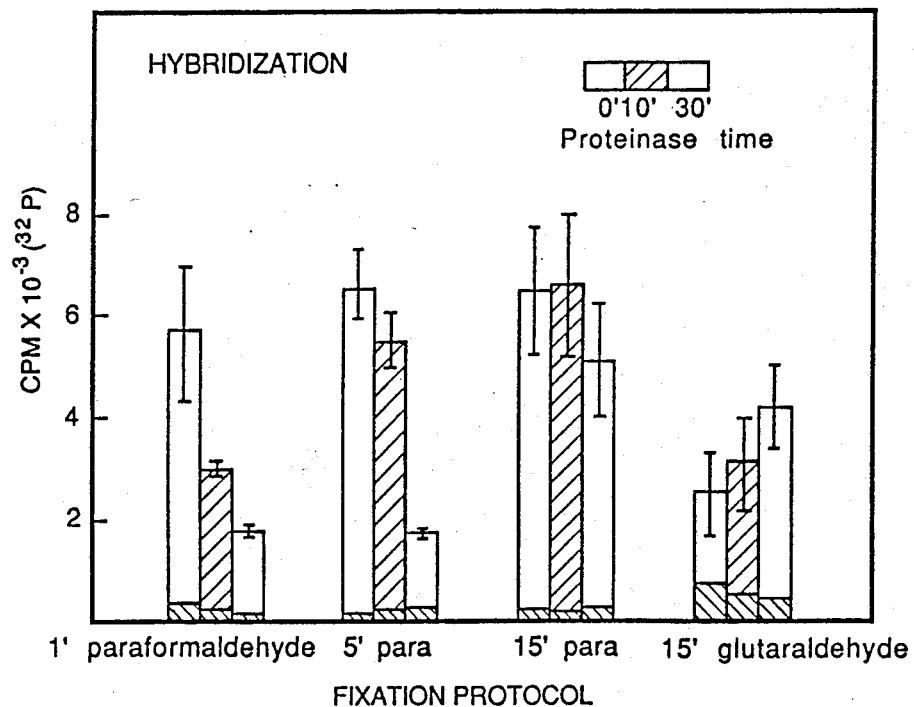

The results of FIG. 2 illustrate that incubation periods as short as 10 minutes with 5 ug/ml proteinase K can cause loss of more than one-half of the total cellular RNA within the cells. This loss of cellular RNA is most marked using paraformaldehyde fixed cells exposed for 1 minute and 5 minute durations and is not a consequence of cells being lost from the coverslips. In comparison, the results of glutaraldehyde fixed samples reveal a very different pattern: Glutaraldehyde protects cellular RNA but cross-links the cytoplasm much more extensively such that less mRNA is available for hybridization (FIG. 2B). If the glutaraldehyde fixed cells are digested with proteinase, the degree of hybridization increases. However, after extensive (30 minute) digestion time of gluteraldehyde fixed cells, the degree of hybridization obtained is substantially lower than for other samples and the background radioactivity is higher than for paraformaldehyde fixed cells which received no proteolytic pretreatment whatsoever. It should be noted that these hybridizations utilize probe fragments of approximately 300 nucleotides in length. Using such small probe sizes, however, it was observed that with glutaraldehyde-fixed cells, proteolytic digestion is necessary to obtain a optimal signal even if probes of smaller sizes were used or the cells less extensively fixed (1% vs. 4% glutaraldehyde) are used. Microscopic examination of these glutaraldehyde fixed cells after proteolysis indicates that the digestion is detrimental and destructive to the cell morphology. The overwhelming conclusion is, therefore, that the use of paraformaldehyde fixation is highly advantageous not only because it provides excellent hybridization efficiency while preserving cellular RNA, but also because it achieves this result with much less degradation of the original cell morphology. These advantages are especially important for in-situ hybridization methodology, since one major goal of this technique is to provide means for obtaining molecular information about the cell while preserving the integrity of the cell itself.

Experimental Series 3: Effects of Hybridization Time

Figure 3A:
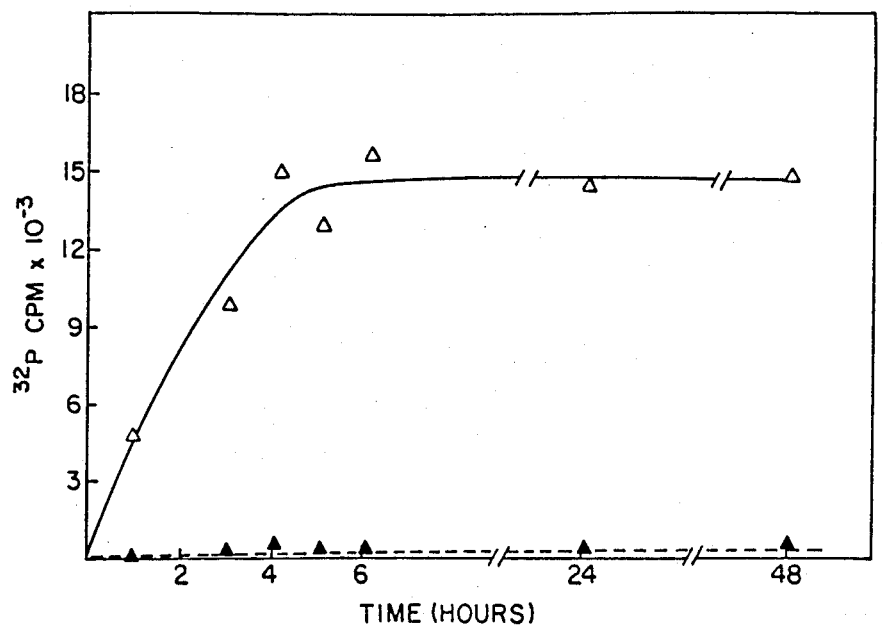
FIGS. 3A and 3B are individual graphs illustrating the effect of increasing hybridization times.
Figure 3B:
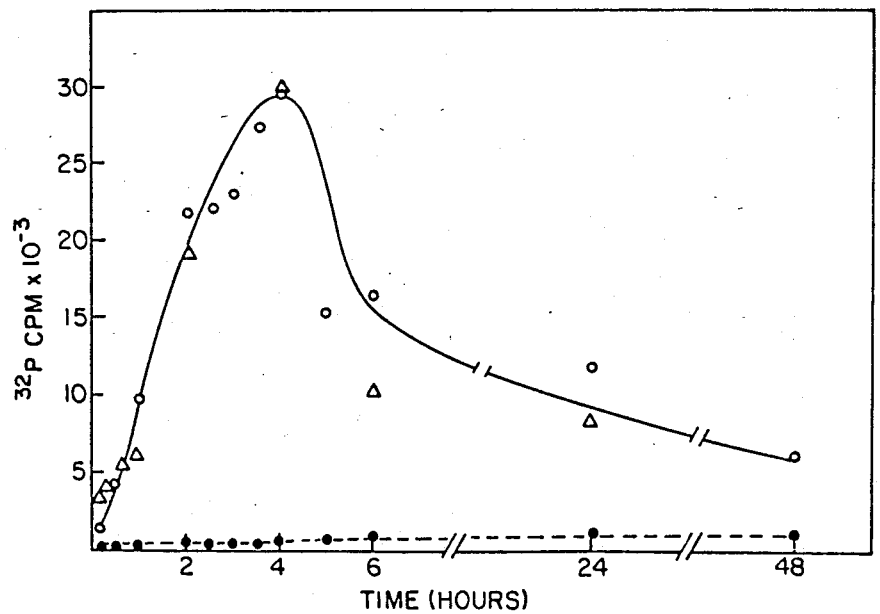

In-situ hybridization techniques well established in this art commonly employed hybridization times ranging from 1-4 days [Zimmerman et al., *Cell* 22:1161-1170 (1983); Jeffrey, W., *J. Cell Biol.* 95:1-7 (1982); Haase et al., *Virology* 119:399-410 (1982)]. Experiments were therefore undertaken to describe the kinetics of our unique in-situ hybridization methodology in order to accurately determine the optimal length of time for the hybridization reaction in-situ. Hybridization, as described herein previously, was allowed to continue to periods up to 48 hours with frequent sampling during the period of 0-6 hours. The data illustrated by FIG. 3 is as follows: open circles and open triangles denote actin probe; closed circles or triangles denote pBR322 control probe. Within FIG. 3A, each point represents an average of six samples. Within FIG. 3B the triangles and circles represent data from two experiments, each of which used triplicate test samples. Within FIG. 3 as a whole, curves are drawn to facilitate visualization of the data and do not represent a theoretical fit. In addition, for each set of data represented, some samples were fixed in paraformaldehyde for 1 minute and some for 15 minute's duration; since there was no consistent difference in results between each of these, the overall results were averaged.

The results of the experimental series consistently demonstrated that hybridization is readily detectable within 10 minutes and is complete within the first 3-4 hours. The data presented in FIGS. 3A and 3B both illustrate that the degree of hybridization increases sharply from the moment of its initiation and reaches a maximum within the first four hours. Because the experimental series utilized 0.6 ug/ml of probe DNA to drive the reaction (DNA excess), the indicated time results are deemed to be independent of the cellular RNA concentration. It should be noted also that if DNA probe concentration were increased to 2.0 ug/ml as recommended, the hybridization reaction would be driven to completion even more rapidly.

In addition, two different results have been observed for hybridization times longer than 24 hours. In some experiments, as illustrated in FIG. 3A, the signal remains relatively constant for two days after achieving a plateau at about 3½ hours' duration. In contrast, by experiments illustrated within FIG. 3B, an unexpected result is observed that hybridization peaks in samples incubated for 3 or 4 hours, but then decreases by 50% or more in identical samples incubated 1-2 days. Results essentially equivalent to these were obtained in three separate experiments using duplicate or triplicate samples for each. It is important to note that this decrease in hybridization with incubation times greater than 24 hours occurred in approximately 20-25% of all experiments and that its occurrence could not be consistently correlated with the technical parameters of fixation time, formamide lot, use of vanadyl sulfate to inhibit RNAse or the use of hybridization buffers for humidifying the incubation chamber. The conclusion is therefore, in instances utilizing prolonged hybridization times greater than 24 hours, the decrease in signal is due to degradation of cellular RNA since (in two of three experiments) there was also a significant decrease in total cellular RNA in samples hybridized for between 1 and 2 days (data not shown).

It is, nevertheless, unquestionable that regardless of the effects of prolonged hybridization duration, the in-situ hybridization reaction is measurable and identifiable within 30 minutes and is quantitatively complete in as little as 3 hours duration. The use of such brief hybridization times is optimal, not only for the sake of efficiency, but because longer periods of incubation introduce a major risk of obtaining a decreased signal as well as a degradation of cell morphology via prolonged exposure of the cell to the hybridization fluid. It should be noted also that in most experiments, as illustrated by FIG. 3B, the background scintillation counts contributed by the control pBR322 probe increases gradually with time - an observation which further favors the use of relatively brief periods for hybridization.

Experimental Series 4: Effects Of Probe Concentration

Figure 4:
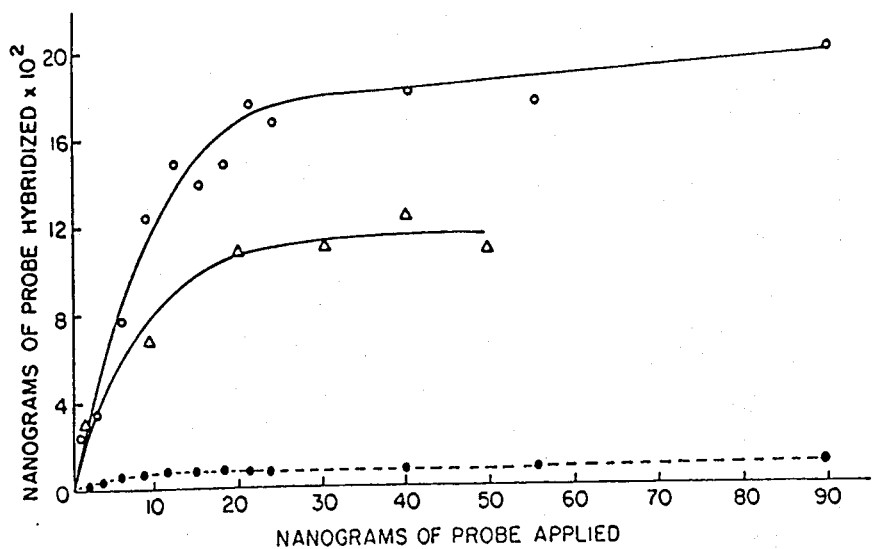
FIG. 4 is a graph illustrating the effect of increasing concentrations of probe on hybridization efficiency.

To determine the amount of actin mRNA which may be detected at saturation levels and to evaluate the effect of probe concentration on signal and background noise, identical samples were incubated with increasing concentrations of actin probe or control pBR322 probe. Hybridization with actin probe was maintained consistently for three hours duration. The results presented within FIG. 4 are the average of three samples each. The circles within FIG. 4 represent hybridization with muscle cultures (myoblasts); the open circles represent the actin probe; the closed circles represent the control pBR322 probe; the triangles represent hybridization of actin probe to fibroblast cultures. Hybridization of the control pBR332 probe to fibroblast cultures was the same as for myotube cultures.

FIG. 4 presents the concentration curves obtained for fibroblasts cultures and for muscle cultures in an early stage of in-vitro differentiation. Both concentration curves show a sharp increase in signal with increasing concentration of probe up to approximately 2.0 ug/ml, after which a much more gradual increase or plateau level is reached. In contrast, background hybridization using the control pBR322 probe shows only a gradual increase in hybridization with increasing probe concentration. Because each of the probes are double stranded DNA, two competing reactions must occur simultaneously: probe cellular mRNA hybridization and probe reannealment. Hence, at any probe concentration, only a fraction of the total probe hybridizes with the RNA within the cell matrix.

In the experimental series using fibroblast cultures, the average number of actin mRNA molecules hybridized per cell can now be calculated from the amount of probe hybridized at saturation and from the empirically determined number of cells in the sample as determined by microscopic cell counts. The quantitative values are thus as follows:

There are estimated to be $2 \times 10^3$ nucleotides in each molecule of actin mRNA [Cleveland et al., Cell 20:95-105 (1980)]; there are $6 \times 10^{23}$ molecules of matter in each mole (avagadro's number); actin mRNA has a density of 330 grams per mole; as empirically shown, there are $1.17 \times 10^{-1}$ nanograms of labeled probe hybridized per sample (FIG. 4); and as empirically determined, there are $1.1 \times 10^5$ cells per test sample (microscopic cell counts).

According therefore:

$$\frac{2 \times 10^3 \text{nucleotides/molecule actin mRNA}}{6 \times 10^{23} \text{ molecules/mole}} \times 330 \text{ grams/mole} = 1.1 \times 10^{-9} \text{ ng/molecule}$$

$$\frac{1.17 \times 10^{-1} \text{ ng/sample}}{1.1 \times 10^{-9} \text{ ng/molecule}} = 1.06 \times 10^8 \text{ molecules actin/sample}$$

$$\frac{1.06 \times 10^8 \text{ molecules/sample}}{1.1 \times 10^5 \text{ cells/sample}} = 9.64 \times 10^2 \text{ molecules actin/fibroblast cell}$$

Hence, as calculated herein, at saturation levels of probe, one is able to detect approximately 964 copies of the 2 kb beta-actin messenger RNA per fibroblast. The reproducibility of these results from saturation experiments was very high, with two other experiments utilizing fibroblasts yielding essentially equivalent results ranging from 900–1,080 copies.

Another experiment was performed using a three day old culture of chicken embryonic myoblasts in which 28% of the cells had differentiated into multinucleated myofibers while the remainder of the cells were fibroblasts or undifferentiated myoblasts. In this experimental series, 0.2 ng of actin probe at saturation level was hybridized with samples containing $8.6 \times 10^4$ cells, corresponding to 2,114 actin messages per cell. The amount of actin in RNA contributed by the differentiated cells is indicated by comparing these results to the data of FIG. 4 for cultures in which none of the cells were differentiated into myofibers. The average number of mRNA for actin per cell was found to be 2.3 fold higher in the differentiating culture which contained a relatively small fraction of differentiated muscle cells (28%). Therefore in a fibroblast culture, one is able to detect approximately 1,000 copies per cell of actin mRNA. In addition, since the number of actin mRNA molecules per cell has been previously quantified at 1,800 copies per fibroblast by solution hybridization [Rothblum, K.N., Biochem. 20:4122–4129 (1981)], the hybridization efficiency of the novel in-situ hybridization method is quantified to be approximately 60%. In view of the fact that prior art hybridization techniques commonly are able to hybridize less than 10% of the targeted sequences, the novel method described herein constitutes a major advance.

Experimental Series 5: Probe Fragment Size

Several studies previously conducted using prior art in-situ hybridization techniques state that the use of small sized DNA fragments as probes (smaller than 200–300 nucleotides in length) is important for successful hybridization to internal nucleic acid sequences within the cells of tissues [Haase et al., *Virology* 119:399–410 (1983); Gee and Roberts, *In DNA* 2, pages 157–163, 1983; Angerer et al., *Nucleic Acids Res.* 9:2819–2840 (1981)]. Experiments investigating the fragment size of the probe used for hybridization after nick-translation have shown the size of the probe fragment to be an important technical parameter.

Figure 5:
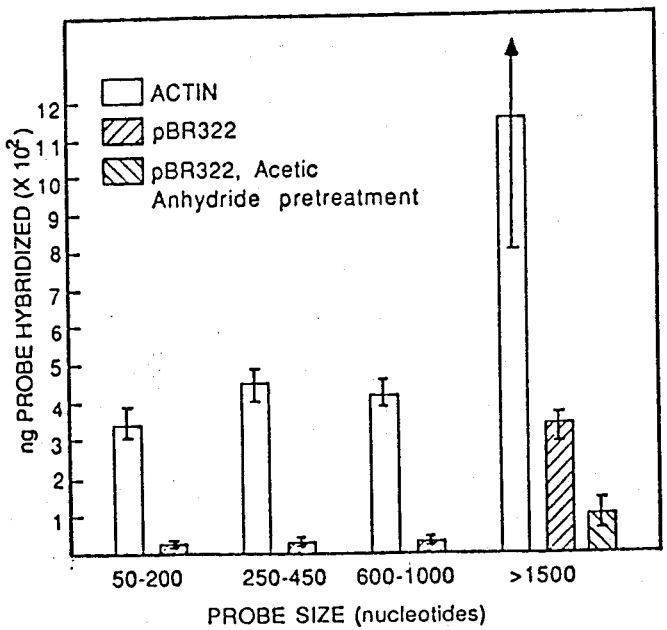
FIG. 5 is a graph illustrating the effect of probe size on hybridization.

The effects of the probe fragment size upon signal and background noise within our preferred in-situ hybridization methodology using paraformaldehyde fixed cells are illustrated by FIG. 5 and represent data from two experiments, each of which utilized duplicate samples. The bars within FIG. 5 indicate the standard deviations. After the actin containing plasmid and the control pPBR322 control plasmid were prepared and radiolabeled using the nick-translation reaction as earlier described, a variety of different sized probe fragments were obtained by varying the amount of DNAse added during the nick-translation reaction sequence. For a given experiment, several nick-translations were performed and the sizes determined by radioautography on alkaline agarose gels using appropriate marker DNA following the conventional procedure. Using quantities from 1 ng/ml–300 ng/ml of DNAse added to the nick-translation reaction, the probe fragment size range was greater than 1,500 nucleotides; whereas larger DNAse concentrations produced fragment sizes as small as 50–200 nucleotides in length. All DNA probes (actin and control) used in a given experiment were nick-translated at the same time and their specific activities (radioactive counts) generally did not differ more than two-fold despite the up to ten-fold differences in average fragment size among them. Several experiments were performed in which probes of different average fragment size were evaluated and it is these results which are presented within FIG. 5.

Within the limits of the probe sizes tested, there is no increase in hybridization with decreasing probe size when using paraformaldehyde fixed cells. There is a slight increase in signal when the probe fragment size is enlarged over 200 nucleotide in length; however, a most striking increase in signal occurs when the probe molecules are very large, above about 1,500 nucleotides in length. The degree of hybridization obtained with probe molecules larger than 1,500 nucleotides in length is on the average 3–4 fold higher than hybridization obtained with molecules less than 1,000 nucleotides in size using equivalent weights of total probe DNA (6 ng/sample; 0.6 ug/ml).

An examination of the individual samples within a given experiment, however, reveals that much larger increases in hybridization are frequently observed. As suggested by the large standard deviation in the data for probe fragments larger than 1,500 nucleotides in length, the increase in signal varied in samples having identical treatments. In some experiments, individual samples had up to 25 fold higher signal than that consistently obtained using smaller probe fragments less than 1000 nucleotides in length. Using only 6 ng total DNA of probe per sample, it was occasionally possible to obtain up to 1 ng of hybridized DNA per sample (using ½ coverslip) from a myotube culture and up to 0.32 ng hybridized DNA for a fibroblast culture. The results greatly exceed the maximum estimates of hybridization expected even for 100% hybridization efficiency! These extremely high signals were not observed with small probe fragments or with the control pBR322 probe, and hybridization of these samples was not reduced by longer rinsing times. The results demonstrate that double-stranded DNA probes of large fragment size (greater than 1500 nucleotides) can significantly amplify the radionuclide signal via formation of "probe networks" at the mRNA target site. This conclusion is further supported by the results presented below.

While the average degree of hybridization with mRNA obtained using DNA probe fragments less than 1,000 nucleotides in size is less than that obtained with very large sized (>1500 nucleotides) DNA probes, the degree of variability in the observed data for smaller fragment sizes is reduced, with the variability largely attributable to differences in the number f cells per sample. When using probe fragments whose lengths are greater than 2,000 nucleotides, there are consistently high background scintillation counts whereas such background noise is relatively negligible when using probe sizes less than 1,500 nucleotides. In addition, the background counts observed with large sized probes can be effectively reduced by pretreatment of the samples in acetic anhydride. In these experiments, prior to hybridization, the samples were immersed for 10 minutes in freshly prepared 0.25% acetic anhydride in triethanolamine buffer, pH 8.0 at room temperature [Angerer et al., *Nucleic Acids Res.* 9:2819–2840 (1981); Hayashi et al., *J. Histochem. Cytochem.* 26:677–679 (1978)]. As illustrated in FIG. 5, the acetic anhydride pretreatment reduced the background of large probe fragments by an average of 70%. This pretreatment was found to have no significant effect on either hybridization efficiency with the actin probe or on the already low background obtained with probe fragments less than 1,500 nucleotides in size (results of two experiments not shown).

Experimental Series 6: Formation of Probe Networks

Figure 6:
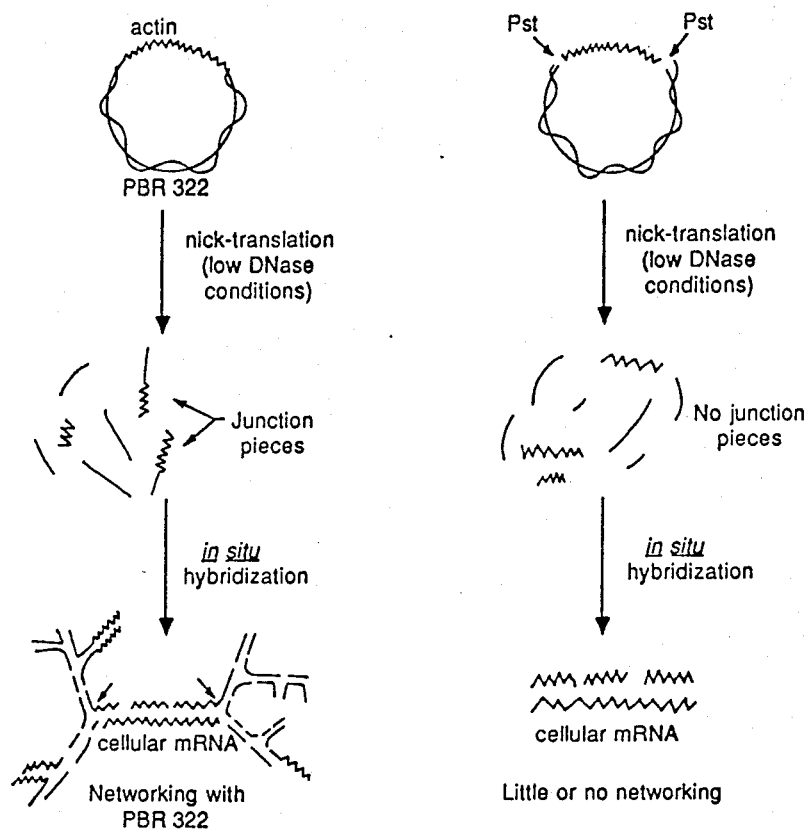
FIG. 6 is a schematic illustration showing the effect of junction pieces in the formation of probe networks.

A series of experiments were undertaken to determine if the formation of probe networks contributes in any significant degree to the efficacy or degree of hybridization obtained. Since the previously described radiolabeled plasmid comprised approximately 4.5 kb of pBR322 DNA nucleotide sequences and 2 kb of actin DNA sequences, the pBR322 DNA sequences should constitute a substantial part of any probe networks that might form. The rationale was to use the restriction enzyme Pst 1 to sever the actin DNA sequences from the pBR322 DNA sequences, thereby eliminating the possibility that the pBR322 DNA sequences could participate in network formation via "junction pieces", a concept introduced to understand the rationale illustrated by FIG. 6. Due to the presence of "junction pieces" which contain both actin and pBR322 sequences, the pBR322 DNA may contribute significantly to signal via the formation of probe networks. Elimination of junction pieces by the Pst 1 digestion prior to nick-translation of the plasmid will greatly reduce network formation. Hence, if very high signals (Cerenkov counts or scintillation counts) are obtained with large (greater than 1500 nucleotides) double-stranded probes are due to the contribution of "junction pieces" to probe network formation, these signals will be markedly reduced by the Pst 1 digestion of the probe and the signals obtained using the Pst 1 cut probe should be considerably less relative to the uncut probe. The empirically obtained data is provided within Table 2.

TABLE 2

| Actin Probe | Fragment Size | Nanograms of Probe Hybridized (Range) |
|---|---|---|
| Uncut | 450 | 0.032 (0.028–0.039) |
| Pst 1 cut | 450 | 0.034 (0.028–0.045) |
| Uncut | 1,500 | 0.302 (0.101–1.05) |
| Pst 1 cut | 1,500 | 0.045 (0.03–0.07) |

As can be seen within Table 2, with relatively small probe fragments averaging 450 nucleotides there is no significant difference in the amount of probe hybridized with Pst 1 cut probes and uncut actin probes. This indicates that, with the probe fragment sizes preferably used in the actin mRNA model test system ranging from approximately 300–500 nucleotides in length, the formation of probe networks does not contribute significantly to the signals obtained. In contrast, with probe fragments averaging 1500 nucleotides (and more) in length, there is a large difference in hybridization signal between the Pst 1 cut probe and the uncut actin probe. The large increase in hybridization signal generally observed with probes of this size (as earlier described) is eliminated when the probe was digested with Pst 1 prior to nick-translation. The results substantiate and confirm the view that unusually high signals obtained with large sized probe fragments represent hybridization to actin mRNA that has been amplified by reannealment of junction pieces at the mRNA target site. Despite a number of attempts towards making probe network formation (with the increase in signal) more reproducible, the extent of signal enhancement using large sized probe continued to vary markedly from sample to sample.

Accordingly, the degree of variation in signal shows that large sized probes which comprise about 75% or more of the nucleotide sequences present in the entirety of the insert DNA should preferably be employed for qualitative studies. In the actin mRNA model test system employing the 2 kb actin insert, such probes are at least 1500 nucleotides in size. Correspondingly, for quantitative studies, the probe will contain less than 50% of the nucleotides sequences that comprise the entirety of the insert DNA. In the model test system using the 2 kb actin insert, it is preferred that probes ranging from 200–500 nucleotides or less be used uniformly because these size fragments do not promote networking. The preparation of large sized probes with the concomittant presence of such "junction pieces" (containing both pBR322 and actin sequences) makes it possible for the signal to be enhanced as much as 25 fold. Because of this powerful amplification, the utility and desirability of such large probes as sensitive, qualitative means for identifying cellular nucleic acids is apparent. Smaller probe fragments, which minimize or eliminate probe networking, provide reproducible, quantitative data for detection of intracellular nucleic acids in instances where precise comparisons of copy number between different types of cells are important.

Experimental Series 7: Biotinated Probes

Figure 7:
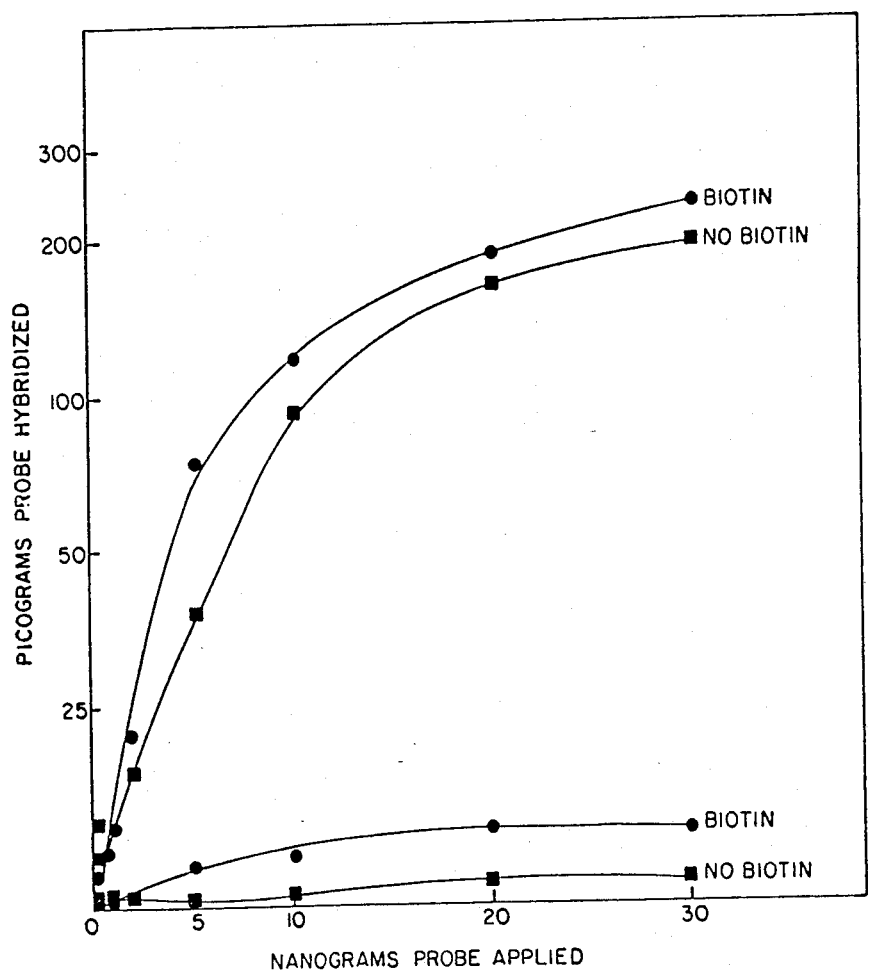
FIG. 7 is a graph illustrating hybridization efficiency using biotin labeled probes and radiolabeled probes.
Figure 8A:
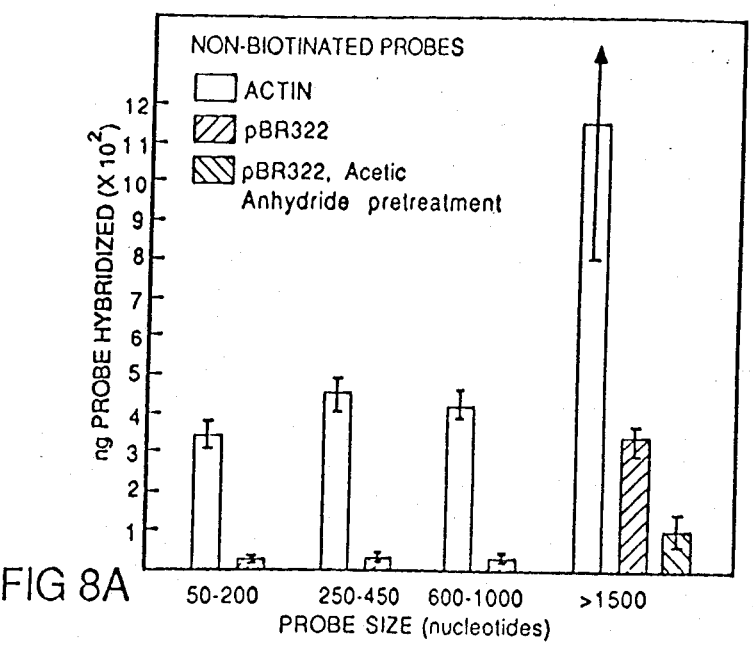
FIGS. 8A and 8B are individual graphs illustrating the effects of probe size upon biotin labeled probes and radionuclide labeled probes.
Figure 8B:
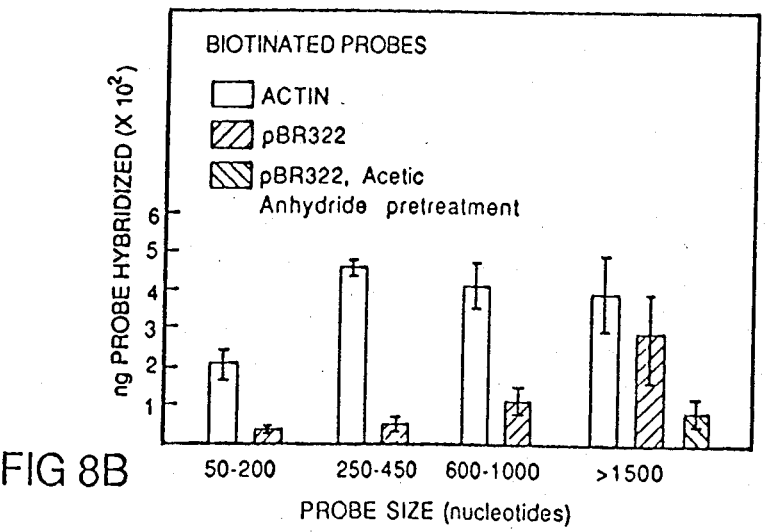

Before testing the use of non-isotopic probes, particularly the use of the biotin-11-dUTP (Enzo Biochemicals, New York), it was deemed important to determine whether any hybridization parameters required alteration due to the presence of the biotin moiety and its linker arm. The results illustrated by FIG. 7 shows that when the probe was labeled with $^{32}P$ and biotin simultaneously and compared with a probe labelled only with $^{32}P$, the saturation kinetics of the hybridization were nearly identical, with the biotinated probe giving a slightly higher background. This indicates that the biotin moiety does not interfere with the quantitative aspects of the hybridization methodology. However, as shown in FIG. 8, it was found that the size of the biotinated probe is critical to obtain a low noise level; the biotinated probe must be smaller than the comparable, non-biotinated probe in order to maintain a good signal-to-noise ratio for quantitative purposes. The preferred size for biotinated probes appears to be approximately 50–200 nucleotides. This also means that networking of biotinated probes may be less likely to occur than with radioactive probes regardless of the probe size. This is confirmed by the lack of signal amplification for biotinated probes greater than 1500 nucleotides in length compared to radiolabeled probes as shown in FIG. 8. In addition, processing the cells through 0.5% triton solution as well as pretreatment of the cells with acetic anhydride just before hybridization also reduces the non-specific binding of biotinated probes.

Experimental Series 8: Other Variable Parameters

A number of other technical parameters were examined for which the results will be stated only briefly herein. Unless otherwise indicated, the data is based upon two or more independent experiments, each of which utilized duplicate or triplicate samples.

(a) Formamide. A parameter found to be of surprising importance was the variability of formamide, the preferred polar ionizing solvent, used for the hybridization reaction. Three experiments were conducted in which formamides from several different sources [Fisher Chemical, MCB, Fluka, Baker] were tested within the preferred hybridization methodology. The results consistently demonstrated up to a 20 fold variation in signal:noise ratio among the different formamides. This is due primarily to dramatic differences in the amount of background counts contributed by the pBR322 control that occurred using different formamides. The extent of hybridization achieved was also affected in some instances but to a much lesser degree. Some of the data indicate that relatively small differences in cellular RNA retention are observed among the different formamides but that primarily the variations among specific lots or batches of formamide is more important than the source of the formamide itself or, in some cases whether or not the formamide had been deionized prior to use. For this reason it is recommended that a single batch of formamide be used uniformly for an entire series of in-situ hybridizations and that sufficient quantities of formamide uniformly prepared as a single lot be used without intermingling or exchange with other lots or sources.

It will be appreciated that formamide variability is one example of a parameter which could not have been examined previous to the existence of the present invention. The quality control aspects for reagents to be used in the in-situ hybridization could not have been realistically achieved in any other known manner.

(b) Sample Dehydration. Some of the hybridization protocols known in the art favor dehydration of the cell or tissue section sample prior to application of the hybridization fluid in order to enhance penetration of probe into the cell or tissues. The effectiveness of this technique was experimentally examined using cultured muscle cells and frozen muscle tissue sections. The samples were processed as earlier described except that they were dehydrated through a series of 70%, 95%, and 100% ethanol and air dried just prior to combination with the hybridization fluid. Under identical conditions, this approach increased the background noise 2-3 fold consistently. Therefore, any dehydration step is deemed to be unnecessary and to be avoided within the preferred in-situ hybridization methodology comprising the present invention.

(c) Isolation of Actin Sequences. These experiments determined whether it was advantageous to utilize probes comprising the actin gene nucleic acid sequences as isolated from the plasmid vector in comparison to the use of the entire plasmid comprising the entirety of both actin nucleic acid sequences and pBR322 nucleic acid sequences. It was found that a higher concentration of actin-pBR322 DNA sequences is required to achieve the same level of hybridization (below saturation levels) as obtained using the actin DNA sequences alone. However, because there was no significant difference in the background noise counts observed with either of the two probes, it is more efficient simply to use the entire pBR322-actin plasmid rather than to isolate the individual actin sequences themselves. Moreover, the presence of the pBR322 DNA sequences may be advantageous if the user desires amplication of the signal via formation of probe networks.

(d) Dextran Sulfate. Conventionally known hybridization techniques utilize dextran sulfate to increase hybridization, presumably by increasing the effective DNA concentration of the hybridization fluid Wahl et al., *PNAS USA* 76:3683-3687 (1979); Wetmur, J. G., *Biopolymers* 14:2517-2524 (1975)]. Our experiments utilized probe molecules of less than 500 nucleotides in length at several non-saturating DNA concentrations. The results demonstrate that use of 5-10% dextran sulfate in the hybridization fluid results in up to a 3 fold increase in hybridization efficiency. In addition, the data indicate that the retention of total cellular RNA in the absence of dextran sulfate was reduced by more than 50% in 3 of 4 experiments. Therefore, the use of dextran sulfate in 5-10% concentrations is preferred to protect mRNA as well as for maximization of the signal.

(e) Rinse Procedure. Many prior art hybridization techniques presume that very extensive rinsing of test samples is necessary after in-situ hybridization, presumably because unhybridized probe remains trapped within the cellular matrix without such extensive washing. Our experimental series tested several different rinse procedures and determined that no advantage is obtained by increasing the rinse time, or the volume of rinse solutions, or the rinse temperature beyond the three individual rinses of 5-30 minutes duration described in the preferred methodology. The background scintillation counts were not reduced by more stringent washes of increased duration or of rinses comprised of other components beyond those described herein. In addition, our experiments noted that the use of brief rinse cycles of five minutes duration each resulted only in a slightly increased background count. Accordingly, the preferred methodology maintains 30 minute rinse cycles as the maximum time for which repeated rinsing should be performed recognizing that a decreased rinse time is likely equally effective.

(f) Pre-hybridization. Conventional filter hybridization procedures require pre-hybridization of the sample with hybridization solution lacking probe DNA to reduce the background noise. The value of such pre-hybridization in the unique in-situ hybridization methodology was tested using a 2-4 hour pre-hybridization period at 37° C. in the hybridization fluid which contained non-specific competitors comprising salmon sperm DNA and *E. Coli* tRNA but lacked probe DNA. Results from three experiments showed no consistent decrease in non-specific binding of the pBR322 control probe as a result of pre-hybridization. This was found to be true with both large (greater than 1,500 nucleotides) and small (200-500 nucleotides) sized molecules.

The present invention is not to be restricted in form nor limited in scope except by the claims appended hereto:

What we claim is:

1. A rapid in-situ hybridization method for detecting, with a non-homopolymer labelled nucleic acid probe, the absence or presence of a target nucleic acid sequence in morphologically intact cells, comprising the steps of:

contacting a sample of said cells with a fixative which preserves and retains the nucleic acids within the cellular morphology of said cells;

contacting the fixed cells with a non-homopolymer labelled probe for not substantially less than ten minutes and not substantially more than 24 hours under conditions whereby said labelled probe penetrates the morphologically intact cells and hybridizes to the target nucleic acid sequence to be detected, if present, said probe consisting essentially of nucleic acid fragments having from about 500 to about 1500 nucleotides and also having an identifying label thereon.

2. A rapid in-situ hybridization method according to claim 1, wherein the fixed cells are contacted with a non-homopolymer labelled probe contained in a hybridization fluid comprising said labelled probe, a non-specific competitor for said labelled probe and an ionizing solvent.

3. An in-situ hybridization method for detecting the presence or absence of a target nucleic acid sequence in morphologically intact cells comprising contacting a sample of cells with a fixative which preserves and retains nucleic acids within the cellular morphology of the cells and contacting the fixed cells with a non-homopolymer labelled probe:

the improvement comprising employing a non-homopolymer labelled probe consisting essentially of labelled nucleic acid fragments having about 500 to about 1500 nucleotides and contacting the sample with the labelled probe for not substantially less than 10 minutes and not substantially more than 24 hours.

* * * * *